US012805834B2

(12) United States Patent
Aliakbari et al.

(10) Patent No.: US 12,805,834 B2
(45) Date of Patent: Nov. 24, 2026

(54) ORAL ULTRASOUND

(71) Applicant: FUJIFILM SONOSITE, INC., Bothell, WA (US)

(72) Inventors: Saeed Aliakbari, Bothell, WA (US); Craig Chamberlain, Bothell, WA (US); Thomas Endres, Bothell, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

(21) Appl. No.: 18/677,624

(22) Filed: May 29, 2024

(65) Prior Publication Data

US 2025/0366821 A1 Dec. 4, 2025

(51) Int. Cl.

*A61B 8/00* (2006.01)
*A61B 8/12* (2006.01)
*G16H 20/40* (2018.01)

(52) U.S. Cl.

CPC .............. *A61B 8/12* (2013.01); *A61B 8/4209* (2013.01); *A61B 8/4488* (2013.01); *A61B 8/5223* (2013.01); *G16H 20/40* (2018.01)

(58) Field of Classification Search

CPC ....... A61B 8/12; A61B 8/4209; A61B 8/4488; A61B 8/5223; G16H 20/40
See application file for complete search history.

(56) References Cited

U.S. PATENT DOCUMENTS

| | | | | |
|---|---|---|---|---|
| 12,491,058 B2 * | 12/2025 | Pesach | ................ | A61C 19/043 |
| 2015/0283277 A1 * | 10/2015 | Schafer | ................ | A61L 2/0029 422/128 |
| 2016/0230007 A1 * | 8/2016 | Johnson | ................ | A63B 71/085 |
| 2020/0281701 A1 * | 9/2020 | Kim | ................ | A61B 8/085 |
| 2021/0343400 A1 * | 11/2021 | Inam | ................ | G16H 10/60 |
| 2022/0202295 A1 * | 6/2022 | Elbaz | ................ | G16H 30/40 |
| 2022/0392645 A1 * | 12/2022 | Wieland | ................ | G16H 50/50 |

* cited by examiner

*Primary Examiner* — Amal Aly Farag
(74) *Attorney, Agent, or Firm* — Womble Bond Dickinson (US) LLP

(57) ABSTRACT

Ultrasound systems, ultrasound scanners, and methods that are used for performing oral procedures. The ultrasound system includes: an ultrasound scanner including a mouth guard configured to transmit ultrasound at a patient anatomy and receive reflections of the ultrasound from the patient anatomy including the patient's teeth. From the reflections, the ultrasound system can generate an assessment of patient health.

21 Claims, 12 Drawing Sheets

1100

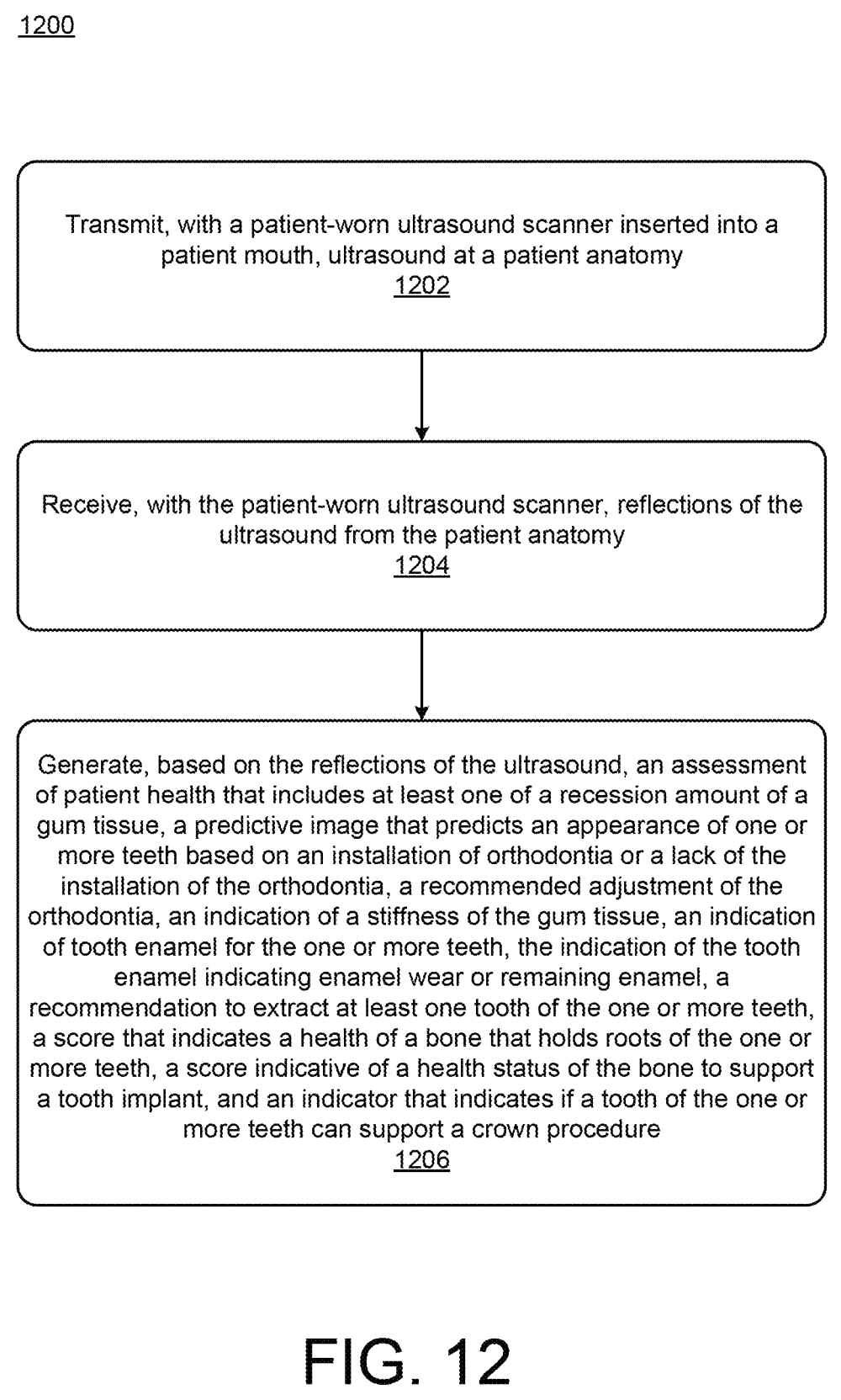

1200

Transmit, with a patient-worn ultrasound scanner inserted into a patient mouth, ultrasound at a patient anatomy
1202

Receive, with the patient-worn ultrasound scanner, reflections of the ultrasound from the patient anatomy
1204

Generate, based on the reflections of the ultrasound, an assessment of patient health that includes at least one of a recession amount of a gum tissue, a predictive image that predicts an appearance of one or more teeth based on an installation of orthodontia or a lack of the installation of the orthodontia, a recommended adjustment of the orthodontia, an indication of a stiffness of the gum tissue, an indication of tooth enamel for the one or more teeth, the indication of the tooth enamel indicating enamel wear or remaining enamel, a recommendation to extract at least one tooth of the one or more teeth, a score that indicates a health of a bone that holds roots of the one or more teeth, a score indicative of a health status of the bone to support a tooth implant, and an indicator that indicates if a tooth of the one or more teeth can support a crown procedure
1206

FIG. 12

ORAL ULTRASOUND

FIELD

Embodiments disclosed herein relate to ultrasound systems. More specifically, embodiments disclosed herein are related to ultrasound devices for use in performing oral procedures.

BACKGROUND

Ultrasound systems can generate ultrasound images by transmitting sound waves at frequencies above the audible spectrum into a body, receiving echo signals caused by the sound waves reflecting from internal body parts, and converting the echo signals into electrical signals for image generation. Because they are non-invasive and non-ionizing, ultrasound systems are used ubiquitously, such as in emergency departments and point of care.

However, oral procedures, including dentistry, orthodontics, and periodontics, rarely use ultrasound imaging and instead rely on ionizing imaging techniques, such as X-ray, thus exposing the patient to cumulative, ionizing radiation. Further, some oral procedures rely on manual measurements. These manual measurements are necessarily subjective and consume resources. For example, recession measurements usually require two operators (one clinician to read calipers and another clinician to record results). Thus, the patient may be subjected to long dental procedures that often consume the time of multiple dentists or dental staff.

SUMMARY

Ultrasound systems, ultrasound scanners, and methods that are used for performing oral procedures are disclosed. In some embodiments, an ultrasound system includes: an ultrasound scanner including a mouth guard configured to, when inserted into a patient mouth to at least partially cover one or more teeth, transmit ultrasound at a patient anatomy and receive reflections of the ultrasound from the patient anatomy; and a processor system coupled to the ultrasound scanner and configured to generate, based on the reflections of the ultrasound, an assessment of patient health.

In some other embodiments, a patient-worn ultrasound scanner has: a mouth guard configured for insertion into a patient mouth; a first transducer array removably attached to a first surface of the mouth guard and configured to transmit ultrasound at a first side of one or more teeth and receive reflections of the ultrasound from the first side of the one or more teeth; and a transceiver configured to transmit ultrasound data based on the reflections to a processor system.

In yet some other embodiments, a method has operations that include inserting a patient-worn ultrasound scanner into a patient mouth; transmitting, with the ultrasound scanner, ultrasound at a patient anatomy; receiving, with the ultrasound scanner, reflections of the ultrasound from the patient anatomy; and generating, based on the reflections of the ultrasound, an assessment of patient health. In some embodiments, the assessment of patient health includes at least one of: a recession amount of a gum tissue; a predictive image that predicts an appearance of one or more teeth based on an installation of orthodontia or a lack of the installation of the orthodontia; a recommended adjustment of the orthodontia; an indication of a stiffness of the gum tissue; an indication of tooth enamel for the one or more teeth, where the indication of the tooth enamel indicates enamel wear or remaining enamel; a recommendation to extract at least one tooth of the one or more teeth; a score that indicates a health of a bone that holds roots of the one or more teeth; a score indicative of a health status of the bone to support a tooth implant; and an indicator that indicates if a tooth of the one or more teeth can support a crown procedure.

Other aspects and advantages of the embodiments will become apparent from the following detailed description taken in conjunction with the accompanying drawings which illustrate, by way of example, the principles of the described embodiments.

BRIEF DESCRIPTION OF THE DRAWINGS

The appended drawings illustrate examples and are, therefore, exemplary embodiments and not considered to be limiting in scope.

FIG. 12 illustrates yet another example method for oral ultrasound in accordance with some embodiments.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Systems, devices, and methods are disclosed herein for oral ultrasound that can use ultrasound systems for imaging. The ultrasound systems can include machine-learned models that process the ultrasound images to generate an assessment of a patient's oral health. The health assessments can include further images (e.g., predictive images to predict results with and without the installation of orthodontia), maps of a patient's oral anatomy, including recession maps and enamel maps, recommendations (e.g., a recommendation to extract a tooth), a grade or score, a binary indicator (e.g., to indicate that a patient's bone can support an implant), and the like.

Example Ultrasound Systems

Figure 1:
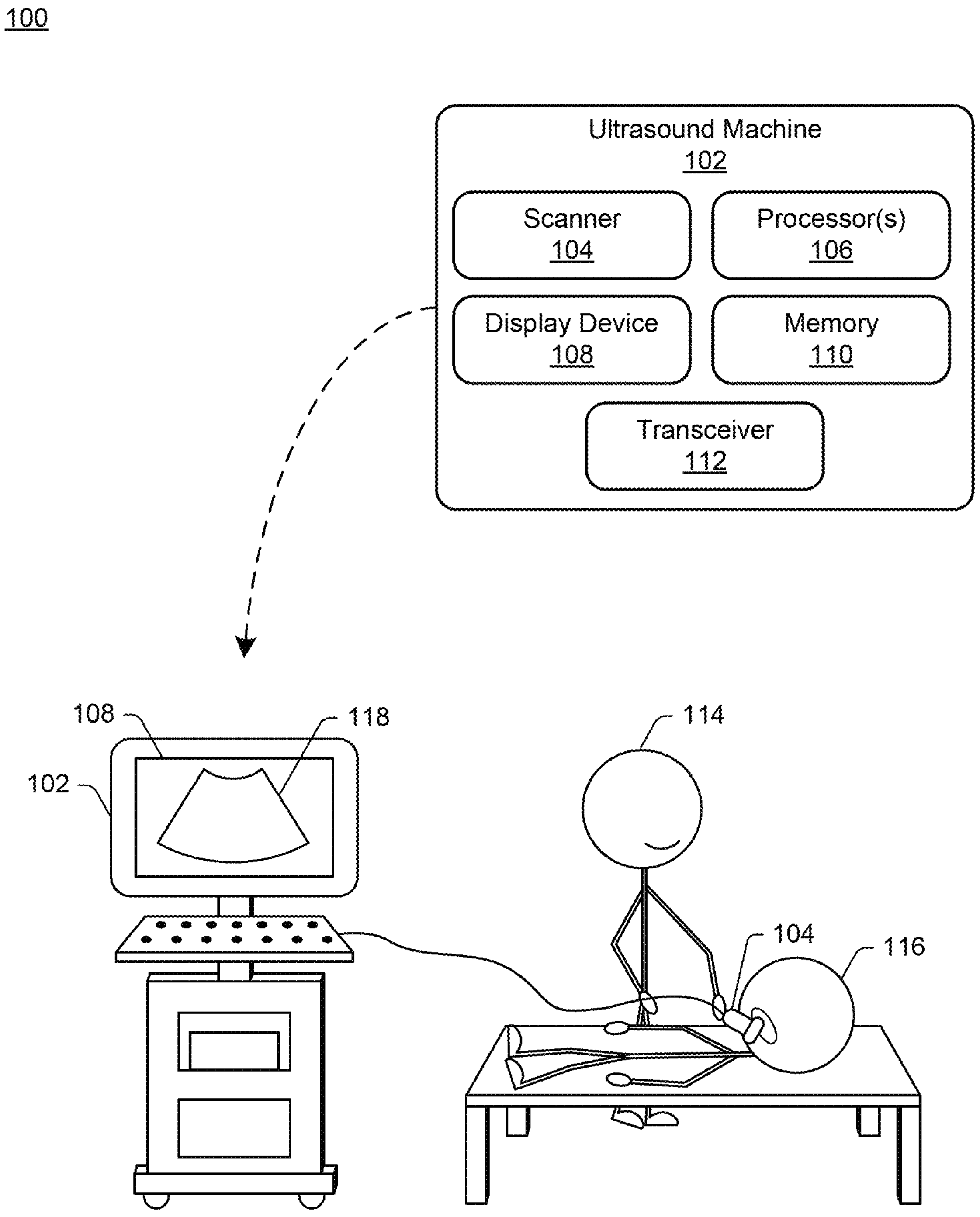
FIG. 1 illustrates an ultrasound system in an environment for oral ultrasound in accordance with some embodiments.

FIG. 1 illustrates an ultrasound system in an environment 100 for oral ultrasound, e.g., at a dentist's office. The ultrasound system in FIG. 1 includes an ultrasound machine 102 and an ultrasound scanner 104. The ultrasound machine 102 generates high-frequency sound waves (e.g., ultrasound) and imaging data based on the ultrasound reflecting off a patient anatomy/body structure that is accessible via the patient's mouth. The ultrasound machine 102 includes various components, some of which include the scanner 104, one or more processors 106, a display device 108, a memory 110, and a transceiver 112.

A user 114 (e.g., dentist, dental hygienist, orthodontist, periodontist, nurse, ultrasound technician, operator, sonographer, clinician, etc.) directs the scanner 104 inside the mouth of a patient 116 to non-invasively scan internal bodily structures (e.g., teeth, gum tissue, bone, sinus cavities, septum, etc.) of the patient 116 for testing, diagnostic, therapeutic, or procedural reasons. In some embodiments, the scanner 104 includes an ultrasound transducer array and electronics communicatively coupled to the ultrasound transducer array to transmit ultrasound signals to the patient's anatomy and receive ultrasound signals reflected from the patient's anatomy. In some implementations, the scanner 104 is an ultrasound scanner, which can also be referred to as an ultrasound probe or transducer. In some embodiments, the scanner 104 is a multi-array scanner.

The display device 108 is coupled to the processor 106, which can include any suitable processor, number of processors, or processor system, such as one or more central processing units (CPUs), graphics processing units (GPUs), vector processors, Reduced Instruction Set Computer (RISC) processors, Reduced Instruction Set Computer (CISC) processors, very long instruction word (VLIW) processors, etc. The processor 106 can execute instructions stored on memory 110 to perform operations disclosed herein for oral ultrasound. For example, the processor 106 can process the reflected ultrasound signals to generate ultrasound data, including an ultrasound image. Further, the processor 106 can implement one or more machine-learned models (e.g., neural networks) to process the ultrasound data and generate an inference including a health assessment (e.g., predictive images to predict results with and without the installation of orthodontia), maps of a patient's oral anatomy, including recession maps and enamel maps, recommendations (e.g., a recommendation to extract a tooth), a grade or score, a binary indicator (e.g., to indicate that a patient's bone can support an implant), and the like.

The display device 108 is configured to generate and display an ultrasound image (e.g., ultrasound image 118) of the anatomy and/or an interventional instrument based on the ultrasound data generated by the processor 106 from the reflected ultrasound signals detected by the scanner 104. In some aspects, the ultrasound data includes the ultrasound image 118 or data representing the ultrasound image 118. The transceiver 112 can be configured to transmit, e.g., over a network maintained by a care facility, the ultrasound data and/or any data related to the ultrasound examination, such as medical worksheet data, to a medical archiver (e.g., a vendor neutral archive (VNA)). In some embodiments, the transceiver 112 can receive data from the medical archiver, such as patient history data or previous examination data.

Figure 2:
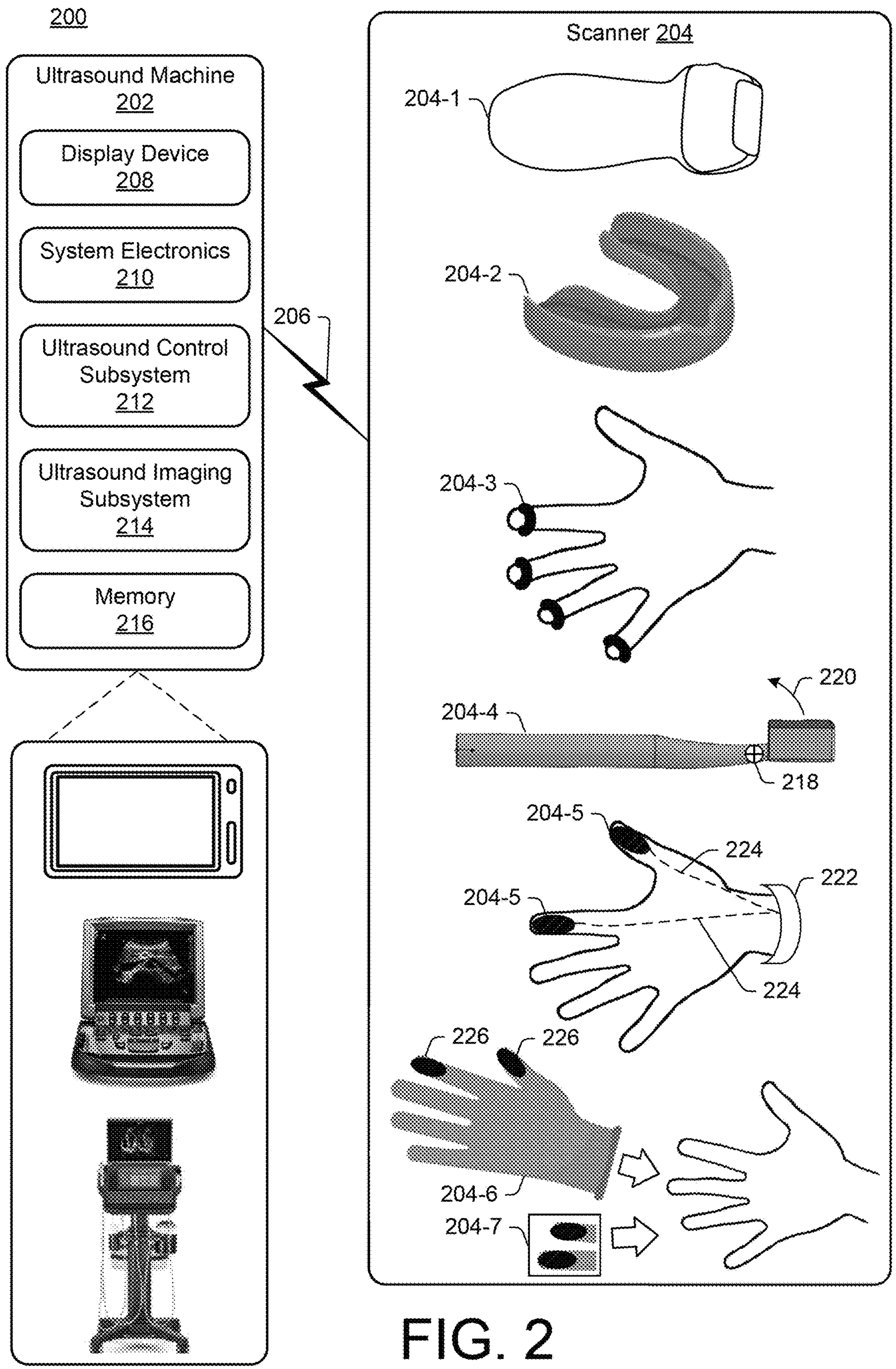
FIG. 2 illustrates an ultrasound system for oral ultrasound in accordance with some embodiments.

FIG. 2 illustrates an example ultrasound system 200 for oral ultrasound in accordance with some embodiments. The ultrasound system 200 is an example of the ultrasound system illustrated in the environment 100 of FIG. 1. Referring to FIG. 2, the ultrasound system 200 includes an ultrasound machine 202 and an ultrasound scanner 204. The ultrasound machine 202 is coupled to the ultrasound scanner 204 via a coupling 206. In some embodiments, the coupling 206 includes one or more cables. Additionally or alternatively, the coupling 206 can include one or more wireless communication links, including one or more wireless transmitters, receivers, or transceivers for communication over a wireless connection or network (e.g., Bluetooth™, Wi-Fi™, etc.).

The ultrasound machine 202 can be of any suitable form factor. Illustrated examples in FIG. 2 include a smart phone (or tablet), a foldable laptop device, and a cart-based device. These devices are meant to be examples and not limiting.

The ultrasound machine 202 includes a display device 208 (which is an example of the display device 108 in FIG. 1). The ultrasound machine 202 also includes system electronics 210. On the scanner 204, a transducer assembly having one or more transducer elements is electrically coupled to the system electronics 210 in the ultrasound machine 202 via the coupling 206. In operation, the transducer assembly transmits ultrasound energy from the one or more transducer elements toward a subject and receives ultrasound echoes from the subject. The ultrasound echoes can be converted into electrical signals by the transducer element(s) and electrically transmitted to the system electronics 210 in the ultrasound machine 102 for processing and generation of one or more ultrasound images.

Capturing ultrasound data from a subject using a transducer assembly generally includes generating ultrasound signals, transmitting ultrasound signals into the subject, and receiving ultrasound signals reflected by the subject. A wide range of frequencies of ultrasound can be used to capture ultrasound data, such as, for example, low-frequency ultrasound (e.g., less than 15 Megahertz (MHz)) and/or high-frequency ultrasound (e.g., greater than or equal to 15 MHz). A particular frequency range to use can readily be determined based on various factors, including, for example, depth of imaging, desired resolution, anatomy being imaged, and so forth. In some embodiments, an ultrasound transducer assembly in accordance uses ultrasound that is greater than or equal to 20 MHz. In some embodiments, an ultrasound scanner in accordance with some embodiments includes multiple transducer arrays. A first transducer array can transmit ultrasound, and a second transducer array can receive reflections of the ultrasound for image generation. In some embodiments, the second transducer array can receive a harmonic of the transmitted frequency (e.g., two or three times the transmitted frequency) to implement super-harmonic imaging. Additionally or alternatively, in some embodiments, the second transducer array can receive a sub-harmonic of the transmitted frequency (e.g., one half or one third of the transmitted frequency) to implement sub-harmonic imaging.

In some implementations, the system electronics 210 include one or more processors (e.g., the processor(s) 106 from FIG. 1), integrated circuits, application-specific integrated circuits (ASICs), Field Programmable Gate Arrays (FPGAs), and power sources to support functioning of the ultrasound machine 202. In some implementations, the ultrasound machine 202 also includes an ultrasound control subsystem 212 having one or more processors. At least one processor, FPGA, or ASIC can cause electrical signals to be transmitted to the transducer(s) of the scanner 204 to emit sound waves and also receives electrical pulses from the scanner 204 that were created from the returning echoes. One or more processors, FPGAs, or ASICs can process the raw data associated with the received electrical pulses and form an image that is sent to an ultrasound imaging subsystem 214, which causes the image (e.g., the image 118 in FIG. 1) to be displayed via the display device 208. Thus, the display device 208 displays ultrasound images from the ultrasound data processed by the processor(s) of the ultrasound control subsystem 212.

In some implementations, the ultrasound machine 202 also includes one or more user input devices (e.g., a keyboard, a cursor control device, a microphone, a camera, touchscreen, etc.) that input data and enable taking measurements from the display device 208 of the ultrasound machine 202. The ultrasound machine 202 can also include a disk storage device (e.g., computer-readable storage media such as read-only memory (ROM), a Flash memory, a dynamic random-access memory (DRAM), a NOR memory, a static random-access memory (SRAM), a NAND memory, and so on) for storing the acquired ultrasound data. In aspects, the disk storage device includes the memory 216, which is local to the ultrasound machine 202. Additionally or alternatively, the memory 216 used for storing the acquisition data can be remote, such as on a remote server communicatively connected to the ultrasound machine 202. In addition, the ultrasound machine 202 can include a printer that prints the image from the displayed data. To avoid obscuring the techniques described herein, such user input devices, disk storage device, and printer are not shown in FIG. 2.

The ultrasound scanner 204 can include various form factors for oral ultrasound. FIG. 2 depicts various examples of the ultrasound scanner 204. The example scanner 204-1 includes a hand-held scanner having a conventional form factor that includes a transducer array that transmits ultrasound through a lens on one end of the scanner 204-1. The scanner 204-1 is therefore suitable for imaging some patient anatomy when inserted inside a patient's mouth, such as the front side of the patient's front teeth. However, this conventional form factor can be difficult to use for other patient anatomies, such as the back side of a patient's front teeth, as this conventional form factor is difficult to orient while inside a patient's mouth so that the ultrasound is directed towards this direction.

Accordingly, the ultrasound scanner 204 includes the example scanner 204-2, which has the form factor of a mouth guard that can be inserted over the bottom or top rows of teeth in a patient's mouth. The ultrasound scanner 204-2 including the mouth guard can include one or more transducer arrays that can transmit ultrasound towards inner and outer sides of the teeth, as well as gums and bone. The ultrasound scanner 204-2 including the mouth guard is discussed in more detail with respect to FIGS. 3-5.

The ultrasound scanner 204 also includes the example scanner 204-3, which has the form factor of one or more rings that can be worn on an operator's fingers. The rings of the example scanner 204-3 can include one or more transducer arrays that can be rigid, flexible, or semi-rigid. The operator can move their fingertips throughout the patient's mouth to image any suitable patient anatomy. In some embodiments, a coupling agent (e.g., water or gel) is inserted into the patient's mouth to couple the acoustic energy between the patient anatomy and the finger-worn transducer array(s). In some embodiments, the operator can pinch two or more fingers around a patient's tooth to simultaneously image two sides of the tooth.

The ultrasound scanner 204 also includes the example scanner 204-4, which has a form factor similar to a conventional tooth brush. The head of the example scanner 204-4 (e.g., where the bristles would be on a conventional tooth brush) can include one or more transducer arrays to transmit and receive ultrasound (e.g., in line with the direction of bristles on a conventional tooth brush). In some embodiments, the example scanner 204-4 includes an articulation joint 218, which allows the head of the example scanner 204-4 to pivot, as indicated by the arrow 220. Hence, by articulating the example scanner 204-4, the ultrasound can be directed to various patient anatomies that would otherwise be difficult to image with a conventional hand held probe, like the back of the patient's front teeth, as previously described with respect to the example scanner 204-1.

In some embodiments, the ultrasound scanner 204 also includes the example scanner 204-5, which has a form factor of wearable patches that can be affixed to an operator's fingertips. The patches can include one or more transducer arrays that can be rigid, flexible, or semi-rigid. Similar to the rings of the example scanner 204-3, the operator can move their fingertips throughout the patient's mouth to image any suitable patient anatomy. Water or gel can be inserted into the patient's mouth as a coupling agent. The patches can be connected to a processor system 222 via one or more wires 224. In some embodiments, the processor system 222 is worn on the operator's wrist, e.g., via a patch, or wristband as illustrated in FIG. 2.

In some embodiments, the ultrasound scanner 204 also includes the example scanner 204-6, which has a form factor of a glove that includes one or more transducer arrays 226 located on the fingertips of the glove. The example scanner 204-6 and the transducer arrays 226 can be operated analogously to the rings of the example scanner 204-3 and/or the wearable patches of the example scanner 204-5, as described above.

In some embodiments, the ultrasound scanner 204 also includes the example scanner 204-7, which has a form factor of finger cups that includes one or more transducer arrays located on the fingertips of the finger cups. The finger cups are configured to be inserted over the fingertips of an operator's hand. The example scanner 204-7 and its transducer arrays can be operated analogously to the rings of the example scanner 204-3 and/or the wearable patches of the example scanner 204-5 and/or the example scanner 204-6, as described above.

In some embodiments of the glove or finger cups, the one or more transducer arrays can include many transducer elements (e.g., 196 elements, etc.) that are operated at a high frequency (e.g., 25-30 MHz) because of the shallow depth that is needed for the oral ultrasound. These arrays can run lengthwise down the finger or glove. Furthermore, one or more of the transducer arrays can comprise 2D arrays, such as, for example, those described above.

Figure 3:
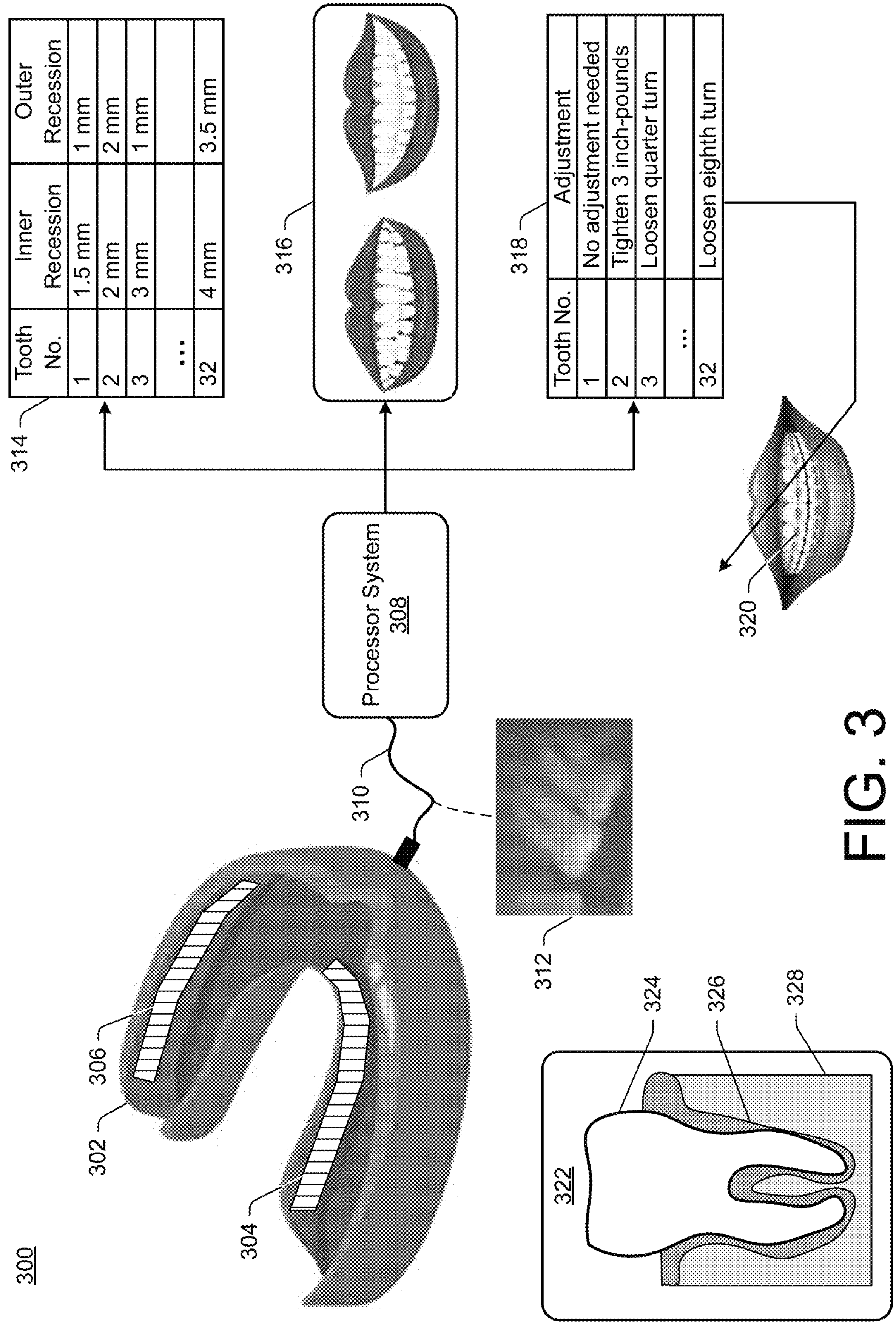
FIG. 3 illustrates an ultrasound system for oral ultrasound in accordance with some embodiments.

FIG. 3 illustrates an example ultrasound system 300 for oral ultrasound in accordance with some embodiments. Referring to FIG. 3, the ultrasound system 300 includes an ultrasound scanner in the form of a mouth guard 302, which is an example of the mouth guard of the example scanner 204-2 in FIG. 2. The mouth guard 302 includes a first transducer array 304 (e.g., an inner array) that is configurable to scan an inside surface of teeth. The mouth guard 302 also includes a second transducer array 306 (e.g., an outer array), that is configurable to scan an outside surface of teeth. The mouth guard 302 is illustrated in FIG. 3 with the two transducer arrays 304 and 306 as examples, and generally can include any suitable number of arrays, e.g., three transducer arrays, four transducer arrays, etc. The transducer arrays 304 and 306 can be removably attached to the mouth guard 302. For example, the transducer arrays 304 and 306 can be inserted into pockets of the mouth guard 302, or attached to a mechanical holder (e.g., a stand or clamp) in the mouth guard 302 (as discussed in more detail below with respect to FIG. 5). In some embodiments, the transducer arrays 304 and 306 include a multi-array structure with transducer elements that can operate at different frequencies. In some embodiments, the transducer arrays 304 and 306 include one or more of the arrays described in U.S. patent application Ser. No. 18/613,694, filed on Mar. 22, 2024, and entitled "Multi-Dimensional and Multi-Frequency Ultrasound Transducers" to Zhang et al., the disclosure of which is incorporated herein by reference in its entirety. In some embodiments, the transducer arrays 304 and 306 include one or more of the arrays described in U.S. patent application Ser. No. 17/561,313, filed on Dec. 23, 2021, and entitled "Array Architecture and Interconnection for Transducers" to Li et al., the disclosure of which is incorporated herein by reference in its entirety. In some embodiments, such multi-array structures can support wider bandwidth and super-harmonic imaging that are not possible with conventional arrays.

In some embodiments, different size transducer arrays are inserted into the mouth guard 302 for different size patients, thereby making the mouth guard 302 more modular. To utilize the mouth guard 302 in this manner, a clinician or assistant can measure a patient with calipers to determine the size of the transducer array to insert into the mouth guard 302. This selection can involve selecting a particular size of mouth guard and different size arrays for different parts of a patient's mouth (e.g., select a No. 2 size array for left, select a No. 4 size array for right, and select a mouth guard to accommodate these choices). Such an arrangement is advantageous to enable the use of an automated process to perform the procedures described herein that can be performed by a less skilled worker (e.g., dental hygienist rather than a dentist, orthopedist, or periodontist). Further, the procedures can be done at a regular dentist office without the need to see the specialist.

The mouth guard 302 is coupled to a processor system 308 via a coupling 310. The processor system 308 is an example of the processors 106 in FIG. 1. In some embodiments, the coupling 310 includes one or more cables to electronically connect the mouth guard 302 and the processor system 308. Additionally or alternatively, the coupling 310 can include a wireless communication link (e.g., Bluetooth™, Wi-Fi™, etc.) to communicatively couple the mouth guard 302 and the processor system 308. The coupling 310 can transfer ultrasound data (e.g., reflections of ultrasound transmitted by one or more of the transducer arrays 304 and 306) to the processor system 308, and the ultrasound data can include ultrasound image data, such as data to generate the ultrasound image 312. In some embodiments, the processor system 308 generates the ultrasound image 312 based on ultrasound data provided to the processor system 308 from the mouth guard 302 (e.g., from one or more of the transducer arrays 304 and 306) over the coupling 310.

Note that while the use of a single mouth guard is described in the examples set forth herein, the techniques disclosed herein extend to simultaneous use of two (upper and lower) mouth guards. In such a case, both mouth guards are connected to a processor. Such an arrangement results in a better workflow with reduced resources as opposed to using only one mouth guard at a time. In some embodiments, to reduce or avoid cross coupling, the frequencies of the arrays are chosen so that they don't interfere with one another. For example, the frequencies can be chosen so they are out of band with respect to one another, or so that their ratio is an irrational number (which would spread the intermodulation energy, reducing spurs). Additionally or alternatively, a separator or divider can be used and inserted between the two mouth guards to reduce or avoid cross coupling.

The transducer arrays 304 and 306 of the mouth guard 302 can be configured to image any suitable patient anatomy when the mouth guard 302 is inserted into a patient mouth and at least partially covers one or more teeth. For example, inset 322 illustrates patient anatomy including a tooth 324, gum tissue 326, and bone 328. Using ultrasound image data representative of one or more of these patient anatomies, the processor system 308 can generate any suitable inference, including an assessment of patient health. For example, the processor system 308 can implement one or more machine-learned models (discussed below in more detail with respect to FIGS. 6 and 7) to generate an assessment of patient health. Examples of an assessment of patient health illustrated in FIG. 3 include a recession table 314, predictive images 316, and adjustment table 318.

The recession table 314 includes, for each tooth, inner recession amounts (e.g., that can be determined from ultrasound data generated by the first transducer array 304), and outer recession amounts (e.g., that can be determined from ultrasound data generated by the second transducer array 306). The recession amounts indicate pocket depths of the gum tissue (e.g., the gum tissue 326) on the inner and outer sides of the teeth (e.g., the tooth 324). Recession can occur when gums become swollen and pull away from the tooth, and can be caused by aggressive brushing, types of foods, smoking, genetics, age, etc. Recession can cause discomfort and expose the tooth to bacteria. Recession is generally not reversible, and requires surgery to correct the problem.

In conventional techniques, recession amounts are manually measured by a first clinician using calipers, who communicates the numbers to a second clinician who writes the numbers down. This process is time consuming, and typically takes up to one quarter the time of a total dentist visit. Further, these conventional techniques are not reliable/consistent, as the measurements are subjective due to operator dependencies. In contrast, the ultrasound system 300 can consistently generate accurate recession amounts in the recession table 314 without operator dependencies. Further, the ultrasound system 300 can generate the recession table 314 almost instantly, and with a single operator (rather than two), which significantly saves resources during the examination and reduces patient discomfort.

The predictive images 316 can include any suitable number of images, from any suitable viewpoint. In FIG. 23, the predictive images 316 include a first image (on the left) and a second image (on the right). The first image illustrates a first predicted appearance of the patient's teeth that could result without an installation of orthodontia, such as braces or a retainer. The second image illustrates a second predicted appearance of the patient's teeth that could result with the installation of the orthodontia. By generating the predictive images 316, the ultrasound system 300 can help the patient determine if the investment in the orthodontia is worth it to the patient. For instance, if the patient does not see a significant difference, or a desired difference, between the first image and the second image, the patient may opt to forego the installation (and associated expense) of the orthodontia.

The adjustment table 318 includes recommended adjustments to orthodontia 320 installed on a patient's teeth. In some embodiments, the ultrasound system 300 can determine the recommended adjustments in the adjustment table 318 by processing, with a machine-learned model, one or more ultrasound images that depict the roots of a tooth and the bone that holds the roots (e.g., as illustrated in inset 322). For instance, the orthodontia 320 can cause the tooth 324 to move in the bone 328. In time, the bone 328 can grow to fill the gap. By monitoring the movement, the system can determine recommended adjustments to the orthodontia 320. In some embodiments, the ultrasound system 300 determines an amount of movement of the roots relative to the bone, or a distance between the roots and the bone, and the recommended adjustment is based on at least one of the amount of the movement and the distance. In some embodiments, the ultrasound system 300 uses ultrasound images from a current examination and additional ultrasound images from a previous examination as inputs to a machine-learned model to determine at least one of the amount of the movement and the distance. In some other embodiments, the ultrasound system 30 uses ultrasound images from a current examination and additional ultrasound images from a previous examination as inputs to a machine-learned model to predict an amount of the movement that can occur based on adjustments in the adjustment table 318 or to predict the adjustments to obtain a particular amount of movement.

In some embodiments, the adjustment table 318 includes the recommended adjustments to the orthodontia 320 for one or more teeth, one or more nodes (e.g., connections) on the orthodontia 320, and the like. In some embodiments, the adjustment table 318 includes an order of the recommended adjustments to orthodontia 320. For instance, the adjustment table 318 can include to adjust the orthodontia 320 for tooth no. 3, followed by an adjustment for tooth no. 8, followed by an adjustment for tooth no. 32, etc. To represent the recommended order of the adjustments, the adjustment table 318 can list the adjustments in the order, or include a number for each tooth, node, or connection that indicates the order.

Note that in some embodiments, the ultrasound images taken by the mouth guard 302 before any adjustments and after each set of adjustments can be used to determine and/or show progress. For example, after each set of adjustments, ultrasound images can be taken and compared to the image of the original location of each tooth or the previous adjustment(s) made with respect to that tooth to determine and then show the amount of movement being made with respect to that tooth.

Figure 4:
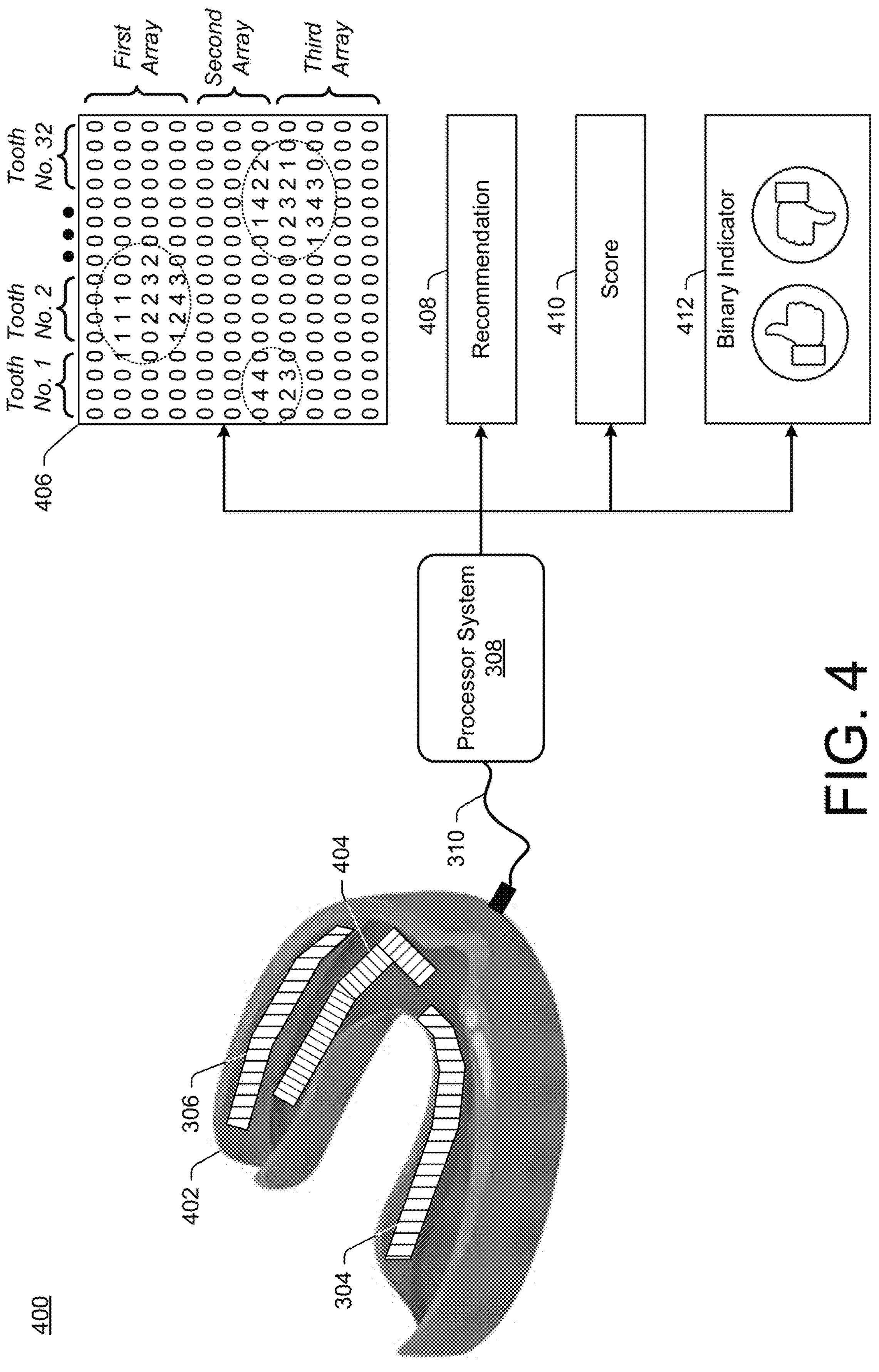
FIG. 4 illustrates an ultrasound system for oral ultrasound in accordance with some embodiments.

FIG. 4 illustrates an example ultrasound system 400 for oral ultrasound in accordance with some embodiments. Referring to FIG. 4, the ultrasound system 400 includes an ultrasound scanner in the form of a mouth guard 402, which is another example of the mouth guard of the example scanner 204-2 in FIG. 2. The mouth guard 402 includes the first transducer array 304 and the second transducer array 306 of the mouth guard 302 in FIG. 3. The mouth guard 402 also includes a third transducer array 404 (e.g., a middle array). The third transducer array 404 is configurable to scan a third surface of teeth (e.g., the bottom side of the teeth when the mouth guard 402 is inserted in the patient's upper row of teeth, or the top side of the teeth when the mouth guard 402 is inserted in the patient's bottom row of teeth). Note that in some embodiments, while note clearly shown, the first transducer array 304, the second transducer array 306 and third transducer array 404 continue around through the length of the mouth guard 402. For example, the first transducer array 304 can continue around the interior of mouth guard 402 to image the interior side of a patient's teeth that faces the tongue, the second transducer array 306 continues around the interior side of mouth guard 402 to image the outer side of a patient's teeth that facing away from the tongue, and the third transducer array 404 continue through the interior bottom of the mouth guard 402.

In some embodiments, using ultrasound image data representative of one or more of patient anatomies, the processor system 308 can generate an assessment of patient health. For example, the processor system 308 can implement one or more machine-learned models (discussed below in more detail with respect to FIGS. 6 and 7) to generate the assessment of patient health. Examples of an assessment of patient health illustrated in FIG. 4 include a map 406, a recommendation 408, a score 410, and a binary indicator 412. In some embodiments, the ultrasound system 400 includes a user interface (not shown for clarity) displayed on a display device (e.g., the display device 108 or the display device 208), and the user interface can provide options for an operator to select one or more machine-learned models to generate the assessment of patient health.

The map 406 can represent any suitable data indicative of a patient's health (e.g., oral health). In some embodiments, the map 406 includes an enamel map that indicates amounts or enamel wear or amounts of remaining enamel on a patient's teeth. For example, the map 406 in FIG. 4 includes an array of integers that can assume values between 0 and 5, inclusive, where a value of 0 can indicate no enamel wear, and a value of 5 can indicate maximum enamel wear (e.g., no remaining enamel). For each tooth, the map 406 includes multiple integers obtained from the ultrasound data for each of the three arrays of the mouth guard 402. For instance, the data from the first transducer array 304 can indicate enamel wear on the inside of the tooth, the data from the second transducer array 306 can indicate enamel wear on the outside of the tooth, and the data from the third transducer array 404 can indicate enamel wear on the bottom or top side of the tooth (e.g., bottom side for upper teeth, and top side for lower teeth). As an example, the map 406 in FIG. 4 indicates three sections of enamel wear, encapsulated by dotted ellipses for clarity. The map 406 indicates enamel wear clustered at tooth no. 2 based on data from the first transducer array 304, and enamel wear clustered at teeth no. 1 and no. 32 based on data from the second transducer array 306 and the third transducer array 404.

In some embodiments, the map 406 indicates amounts of remaining enamel. For instance, a value of 0 can indicate no remaining enamel, and a value of 5 can indicate maximum remaining enamel (e.g., no enamel wear). In some embodiments, the map 406 indicates a property of the teeth other than enamel or enamel wear, including cavity locations (with the integers in the map indicating the depths of the cavities), cracks in the teeth, teeth that have had previous repairs done, such as a crown, filling, veneer, etc.

In some embodiments, the map 406 indicates a property of the bone holding the teeth (e.g., the bone 328 in FIG. 3). The property of the bone can include one or more of bone wear, surface texture (e.g., roughness) of the bone, porosity of the bone, contour of the bone (e.g., high spots or spikes can elevate the gum tissue and permit the entrance of bacteria), osteoporosis, and the like.

In some embodiments, the map 406 indicates a property of the gum tissue (e.g., the gum tissue 326 in FIG. 3). The property of the gum tissue can include one or more of a stiffness and/or elasticity of the gum tissue, a discoloration and/or contrast level of the gum tissue (which can indicate a lesion or bacteria concentration), areas of the gum tissue that have had previous repairs done (such as a graft), areas with lesions or cancers, and the like.

The recommendation 408 can represent any suitable recommendation for a clinician and/or the patient to perform. An example of the recommendation 408 that can be generated by the ultrasound system based on the ultrasound data from one or more of the first transducer array 304, the second transducer array 306, and the third transducer array 404 includes a recommendation to extract (e.g., pull or remove) a tooth. The recommendation can be based on the health of the gum tissue surrounding the tooth.

Other examples of the recommendation 408 include a recommendation to perform a crown procedure, a recommendation to fill a cavity, a recommendation to install orthodontia, a recommendation to generate adjustments for orthodontia (e.g., a recommendation to generate the adjustment table 318 in FIG. 3), and the recommended adjustments themselves. Still other examples of the recommendation 408 include a recommendation to see a specialist, such as an orthodontist or periodontist, a recommendation to prescribe an oral prosthetic, such as a protective mouth guard, for patient wear when sleeping, to prevent teeth grinding, and the like.

The score 410 can include any suitable score or grade for any suitable data indicative of a patient's health (e.g., oral health). In some embodiments, the score 410 includes a score that indicates a health of a bone (e.g., the bone 328 in FIG. 3) that holds (e.g., supports) the roots one or more teeth. The score can be based on an amount of movement of the roots relative to the bone or a distance between the roots and the bone Additionally or alternatively, the score 410 can be indicative of a health status of the bone to support a tooth implant. Additionally or alternatively, the score 410 can indicate if a tooth can support a crown procedure. Additionally or alternatively, the score 410 can be indicative of the health status of gum tissue. The score can be based on the tissue stiffness or elasticity, and/or an amount of contrast of the gum tissue. In some embodiments, the score 410 includes a binary score. Alternatively, the score can have more than two values, such as a scale between one and five, or one and ten, or one and three, etc.

The binary indicator 412 can include any suitable binary indicator for any suitable data indicative of a patient's health (e.g., oral health). The binary indicator 412 can include an icon (e.g., thumbs up or thumbs down), a number (e.g., zero or one), text ("yes" or "no"), a color (e.g., red or green), and the like to indicate a binary value. For example, the binary indicator 412 can indicate to extract or not to extract a tooth, that a bone can or cannot support an implant, that a tooth can or cannot support a crown procedure, and the like. The ultrasound system can display the binary indicator 412 on a display device (e.g., the display device 108 or the display device 208).

Figure 5:
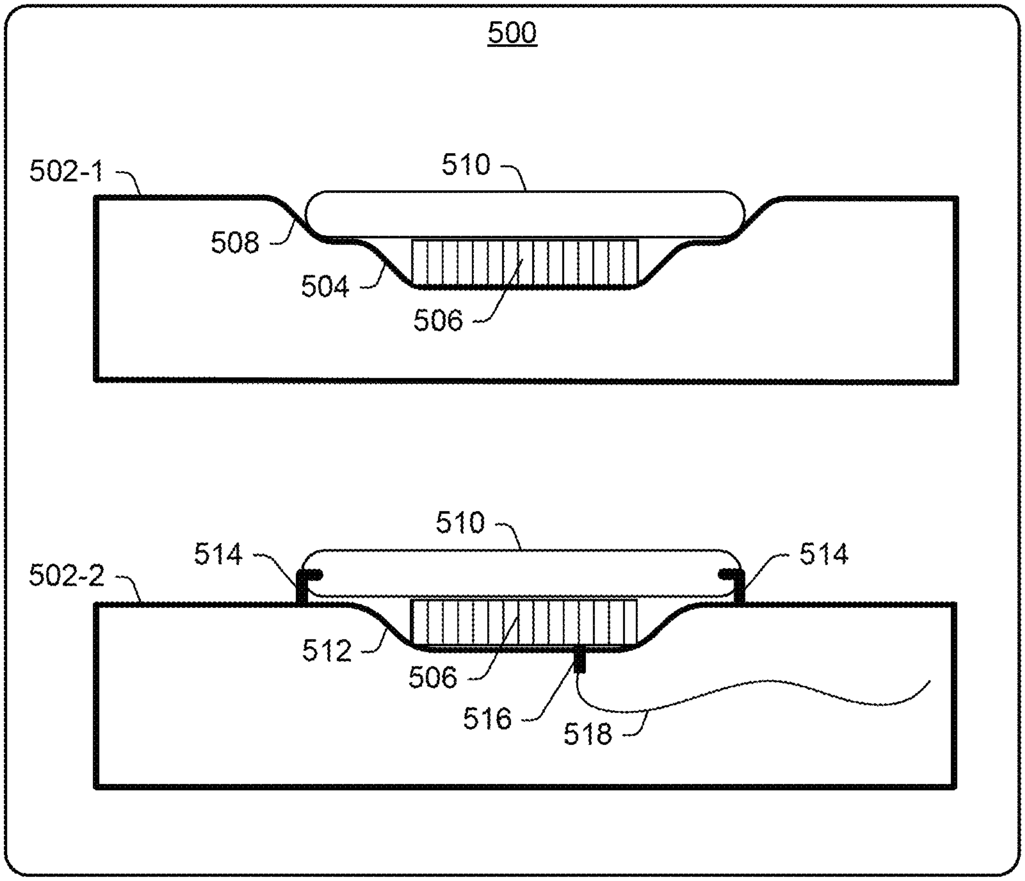
FIG. 5 illustrates example profiles of ultrasound scanners in accordance with some embodiments.

FIG. 5 illustrates profiles 500 of ultrasound scanners in accordance with some embodiments. Referring to FIG. 5, profiles 500 include a profile 502-1 of a first ultrasound scanner and a profile 502-2 of a second ultrasound scanner. The first ultrasound scanner and the second ultrasound scanner are examples of the ultrasound scanner 204 in FIG. 2. In some embodiments, the first ultrasound scanner and the second ultrasound scanner are examples of mouth guards in accordance with some embodiments, such as the mouth guard of the ultrasound scanner 204-2, and the mouth guards 302 and 402.

The ultrasound scanner indicated at profile 502-1 includes a first pocket 504 configured to hold a transducer array 506. The transducer array 506 is an example of a transducer array of an ultrasound scanner (e.g., a mouth guard), such as one of the first transducer array 304 and the second transducer array 306. Although the viewpoint is a profile viewpoint in FIG. 5, one skilled in the art would understand that if the profile viewpoint is instead considered a bird's eye viewpoint, then the transducer array 506 is also an example of the third transducer array 404.

The ultrasound scanner shown at profile 502-1 also includes a second pocket 508 configured to hold a coupling agent 510. The coupling agent 510 can be encapsulated in a packet (e.g., a gel pack). Alternatively, the coupling agent 510 can lack a bounding container, like a packet, and instead be a gel (e.g., hydrogel, etc.) or paste that maintains its shape through its consistency, the second pocket 508, and the transducer array 506. The second pocket 508 positions the coupling agent 510 between the transducer array 506 and a patient anatomy, so that the coupling agent 510 couples ultrasound from the transducer array 506 to the patient anatomy, as well as reflections of the ultrasound from the patient anatomy back to the transducer array 506. In some embodiments, the coupling agent 510 includes a biocompatible material that is acoustically transparent. In some embodiments, the coupling agent 510 is coupled to the transducer array 506.

The ultrasound scanner shown at profile 502-2 is an alternative embodiment from that indicated at the profile 502-1. The ultrasound scanner shown at profile 502-2 includes a pocket 512 configured to hold the transducer array 506. However, rather than including another pocket to hold the coupling agent 510, the ultrasound scanner indicated at profile 502-2 includes stands 514 implemented to attach to a pad containing the coupling agent 510. The stands can retain the pad containing the coupling agent 510 via pressure. In some embodiments, the ultrasound scanner shown at profile 502-2 also includes a connector 516 (which can include one or more connectors) to electronically couple the transducer array 506 to an ultrasound machine, processor system, etc., via a wire 518 that can be embedded within the ultrasound scanner/mouth guard. In some embodiments, the wire 518 includes one or more wires, one of which can carry power to the transducer array 506. The power source that provides the power can include a battery.

In some embodiments, the coupling agent 510 includes a hardening agent that when activated by an activation source causes the coupling agent 510 to harden into a mold. Examples of the activation source include a heat gun, an ultraviolet light, a chemical configured to be injected into the coupling agent 510, and the like. The mold can represent one or more teeth and/or gum tissue between teeth (e.g., where teeth are missing). The ultrasound system can generate a three-dimensional (3D) model of the mold, and a model of a bridge based on the 3D model. A bridge is a prosthetic device that replaces one or more missing teeth, and can attach to, or abut against, remaining teeth in the patient's mouth to stay in place. Hence, the mold can represent the missing teeth, remaining teeth that a bridge can attach to, and/or gum tissue. The ultrasound system can include a 3D printer configured to generate the bridge from the 3D model. In some embodiments, the coupling agent 510 includes a whitening agent configured to whiten the patient's teeth.

Example Machine-Learned Models

Many of the aspects described herein can be implemented using a machine-learned model. For the purposes of this disclosure, a machine-learned model is any model that accepts an input, analyzes and/or processes the input based on an algorithm derived via machine-learning training, and provides an output. A machine-learned model can be conceptualized as a mathematical function of the following form:

$$f(\hat{s}, \theta) = \hat{y} \quad \text{Equation (1)}$$

In Equation (1), the operator f represents the processing of the machine-learned model based on an input and providing an output. The term ŝ represents a model input, such as ultrasound data. The model analyzes/processes the input ŝ using parameters θ to generate output ŷ (e.g., object identification, object segmentation, object classification, etc.). Both ŝ and ŷ can be scalar values, matrices, vectors, or mathematical representations of phenomena such as categories, classifications, image characteristics, the images themselves, text, labels, or the like. The parameters θ can be any suitable mathematical operations, including but not limited to applications of weights and biases, filter coefficients, summations or other aggregations of data inputs, distribution parameters such as mean and variance in a Gaussian distribution, linear algebra-based operators, or other parameters, including combinations of different parameters, suitable to map data to a desired output.

Figure 6:
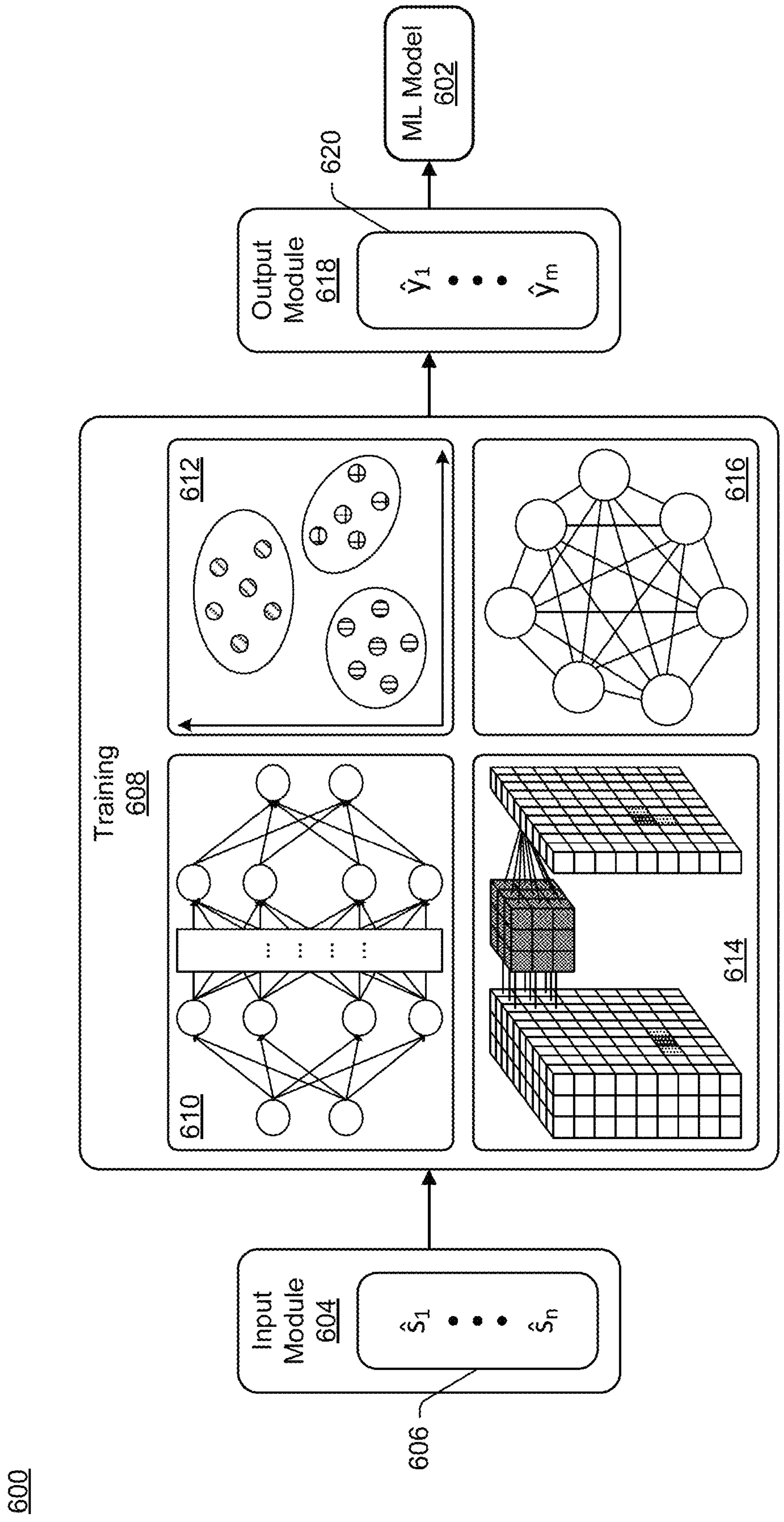
FIG. 6 illustrates some embodiments of a machine-learned model.

FIG. 6 represents an example machine-learning architecture 600 used to train a machine-learned model M 602. An input module 604 accepts an input ŝ 606, which can be an array with members ŝ1 through ŝn. The input ŝ 606 is fed into a training module 608, which processes the input ŝ 606 based on the machine-learning architecture 600. For example, if the machine-learning architecture 600 uses a multilayer perceptron (MLP) model 610, the training module 608 applies weights and biases to the input ŝ 606 through one or more layers of perceptrons, each perceptron performing a fit using its own weights and biases according to its given functional form. MLP weights and biases can be adjusted so that they are optimized against a least mean square, logcosh, or other optimization function (e.g., loss function) known in the art. Although an MLP model 610 is described here as an example, any suitable machine-learning technique can be employed, some examples of which include but are not limited to k-means clustering 612, convolutional neural networks (CNN) 614, a Boltzmann machine 616, Gaussian mixture models (GMM), and long short-term memory (LSTM). The training module 608 provides an input to an output module 618. The output module 618 analyzes the input from the training module 608 and provides an output in the form of ŷ 620, which can be an array with members ŷ1 through ŷm. The output ŷ 620 can represent a known correlation with the input ŝ 606, such as, for example, object identification, segmentation, and/or classification.

In some embodiments, the input ŝ 606 can be or include a training input labeled with known output correlation values, and these known values can be used to optimize the output ŷ 620 in training against the optimization/loss function. In some embodiments, the machine-learning architecture 600 can categorize the output ŷ 620 values without being given known correlation values to the inputs ŝ 606. In some embodiments, the machine-learning architecture 600 is a combination of machine-learning architectures. By way of example, a first network can use the input ŝ 606 and provide the output ŷ 620 as an input ŝML to a second machine-learned architecture, with the second machine-learned architecture providing a final output ŷf. In some other embodiments, one or more machine-learning architectures are implemented at various points throughout the training module 608.

In some machine-learned models, all layers of the model are fully connected. For example, all perceptrons in an MLP model act on every member of ŝ. For an MLP model with a 100×100 pixel image as the input, each perceptron provides weights/biases for 10,000 inputs. With a large, densely layered model, this may result in slower processing and/or issues with vanishing and/or exploding gradients. A CNN, which may not be a fully connected model, can process the same image using 5×5 tiled regions, requiring only 25 perceptrons with shared weights, giving much greater efficiency than the fully connected MLP model.

Figure 7:
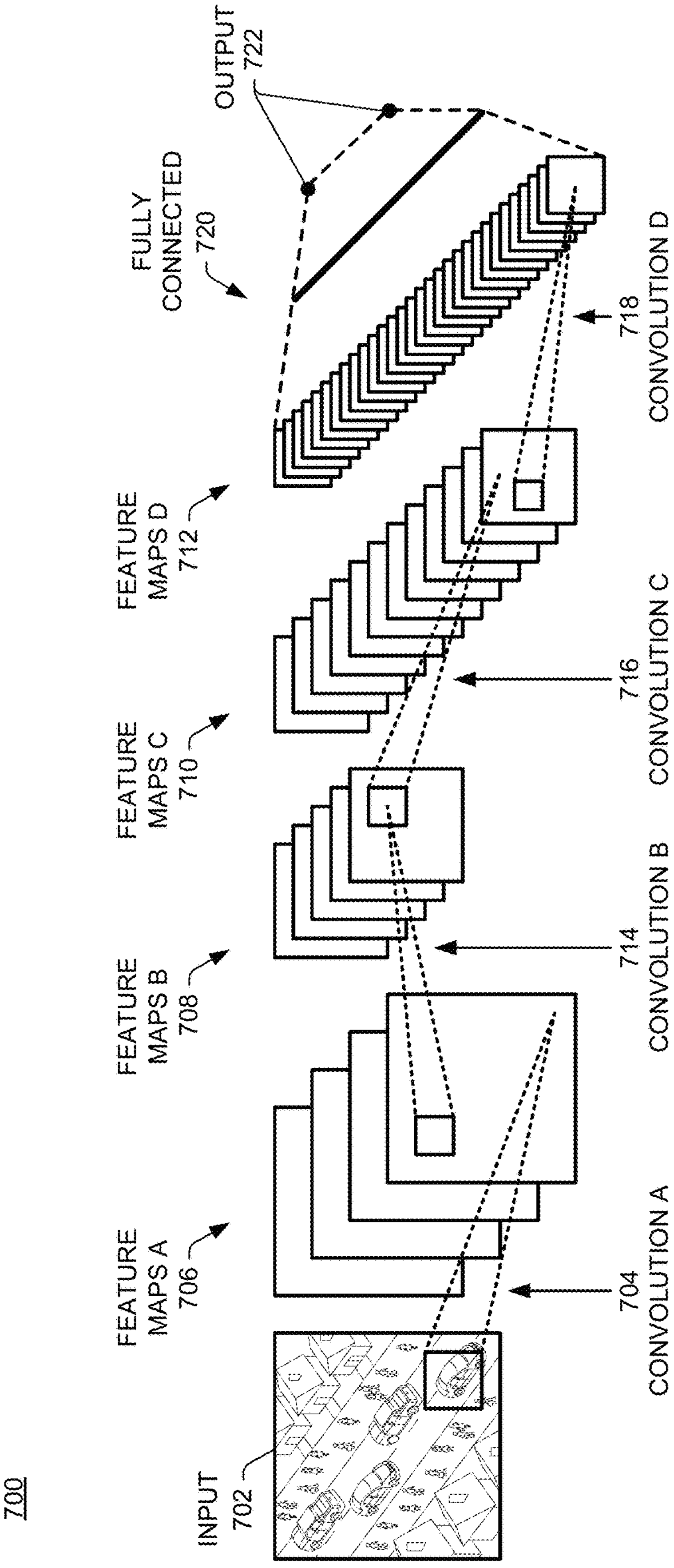
FIG. 7 illustrates some embodiments of a neural network.

FIG. 7 represents an example model 700 using a CNN to process an input image 702, which includes representations of objects that can be identified via object recognition, such as people or cars (or an anatomy). Convolution A 704 can be performed to create a first set of feature maps (e.g., feature maps A 706). A feature map can be a mapping of aspects of the input image 702 given by a filter element of the CNN. This process can be repeated using feature maps A 706 to generate further feature maps B 708, feature maps C 710, and feature maps D 712 using convolution B 714, convolution C 716, and convolution D 718, respectively. In this example, the feature maps D 712 become an input for fully connected network layers 720. In this way, the machine-learned model can be trained to recognize certain elements of the image, such as people, cars, or a particular patient anatomy, and provide an output 722 that, for example, identifies the recognized elements. In some aspects, a feature vector and/or inference generated with an ultrasound system can be appended to a feature map (e.g., feature map B 708) generated by a neural network (e.g., CNN). In this way, the feature vector and/or inference can be used as a secondary/conditional input to the neural network.

Although the example of FIG. 7 shows a CNN as a part of a fully connected network, other architectures are possible and this example should not be seen as limiting. There can be more or fewer layers in the CNN. A CNN component for a model can be placed in a different order, or the model can contain additional components or models. There may be no fully connected components, such as a fully convolutional network. Additional aspects of the CNN, such as pooling, downsampling, upsampling, or other aspects known to people skilled in the art can also be employed.

An Example Device

Figure 8:
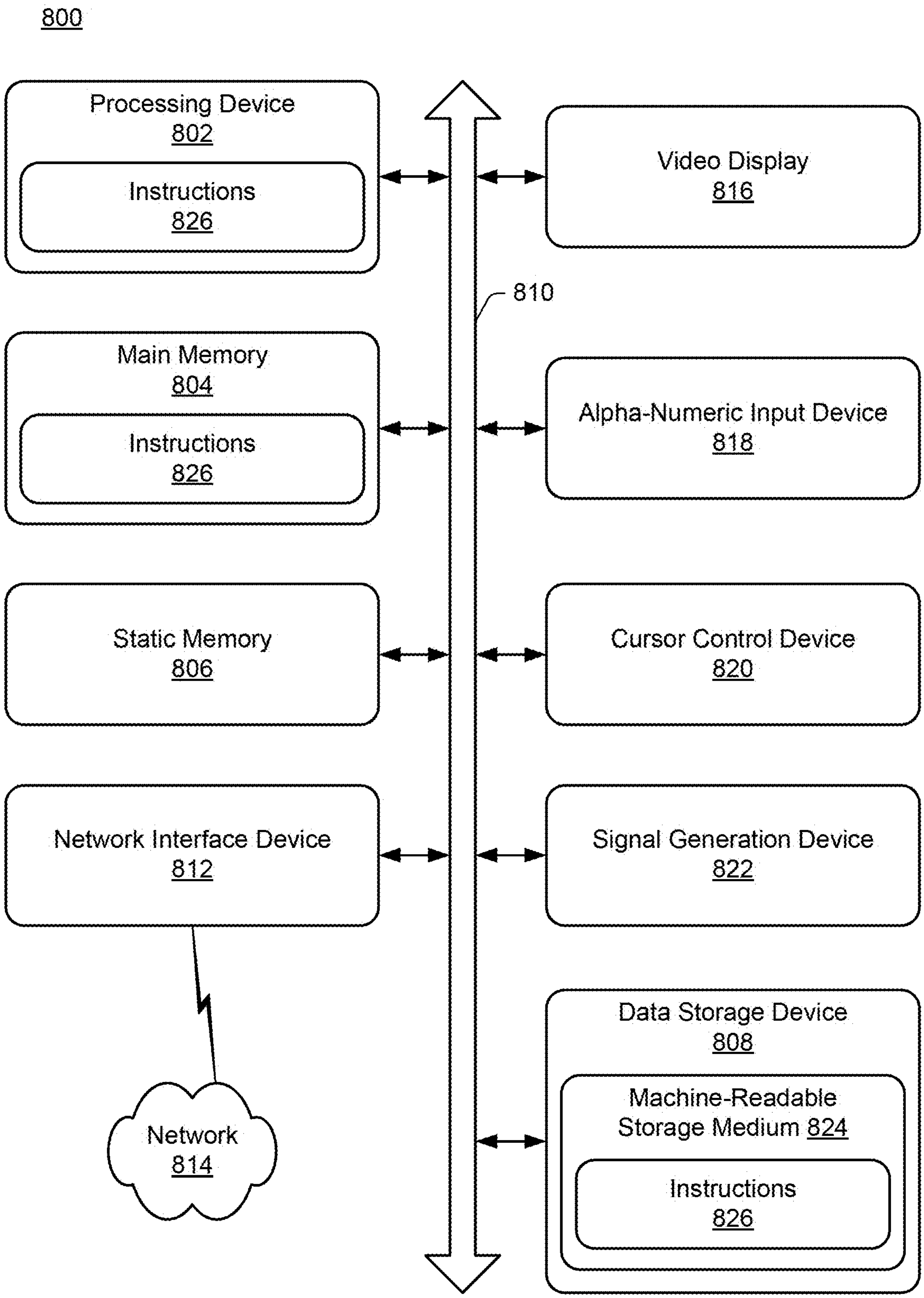
FIG. 8 illustrates an example device for oral ultrasound in accordance with some embodiments.

FIG. 8 illustrates a block diagram of an example computing device 800 that can perform one or more of the operations described herein, in accordance with some implementations. Referring to FIG. 8, the computing device 800 can be connected to other computing devices in a local area network (LAN), an intranet, an extranet, and/or the Internet. The computing device can operate in the capacity of a server machine in a client-server network environment or in the capacity of a client in a peer-to-peer network environment. The computing device can be provided by a personal computer (PC), a server computer, a desktop computer, a laptop computer, a tablet computer, a smartphone, an ultrasound machine, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein. In some implementations, the computing device 800 is one or more of an ultrasound machine, an ultrasound scanner, an access point, a charging station, and a medical archiver.

The example computing device 800 can include a processing device 802 (e.g., a general-purpose processor, a programmable logic device (PLD), etc.), a main memory 804 (e.g., synchronous dynamic random-access memory (DRAM), read-only memory (ROM), etc.), and a static memory 806 (e.g., flash memory, a data storage device 808, etc.), which can communicate with each other via a bus 810. The processing device 802 can be provided by one or more general-purpose processing devices such as a microprocessor, a central processing unit, or the like. In an illustrative example, the processing device 802 comprises a complex instruction set computing (CISC) microprocessor, a reduced instruction set computing (RISC) microprocessor, a very long instruction word (VLIW) microprocessor, or a processor implementing other instruction sets or processors implementing a combination of instruction sets. The processing device 802 can also comprise one or more special-purpose processing devices such as an application-specific integrated circuit (ASIC), a field programmable gate array (FPGA), a digital signal processor (DSP), a network processor, or the like. The processing device 802 can be configured to execute the operations described herein, in accordance with one or more aspects of the present disclosure, for performing the operations and steps discussed herein.

The computing device 800 can further include a network interface device 812, which can communicate with a network 814. The computing device 800 also can include a video display unit 816 (e.g., a liquid crystal display (LCD), an organic light-emitting diode (OLED), a cathode ray tube (CRT), etc.), an alphanumeric input device 818 (e.g., a keyboard), a cursor control device 820 (e.g., a mouse), and an acoustic signal generation device 822 (e.g., a speaker, a microphone, etc.). In one embodiment, the video display unit 816, the alphanumeric input device 818, and the cursor control device 820 can be combined into a single component or device (e.g., an LCD touch screen).

The data storage device 808 can include a computer-readable storage medium 824 on which can be stored one or more sets of instructions 826 (e.g., instructions for carrying out the operations described herein, in accordance with one or more aspects of the present disclosure). The instructions 826 can also reside, completely or at least partially, within the main memory 804 and/or within the processing device 802 during execution thereof by the computing device 800, where the main memory 804 and the processing device 802 also constitute computer-readable media. The instructions can further be transmitted or received over the network 814 via the network interface device 812.

Various techniques are described in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. In some aspects, the modules described herein are embodied in the data storage device 808 of the computing device 800 as executable instructions or code. Although represented as software implementations, the described modules can be implemented as any form of a control application, software application, signal-processing and control module, hardware, or firmware installed on the computing device 800.

While the computer-readable storage medium 824 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding, or carrying a set of instructions for execution by the machine and that causes the machine to perform the methods described herein. The term "computer-readable storage medium" shall accordingly be taken to include, but not be limited to, solid-state memories, optical media, and magnetic media.

Example Environment

Figure 9:
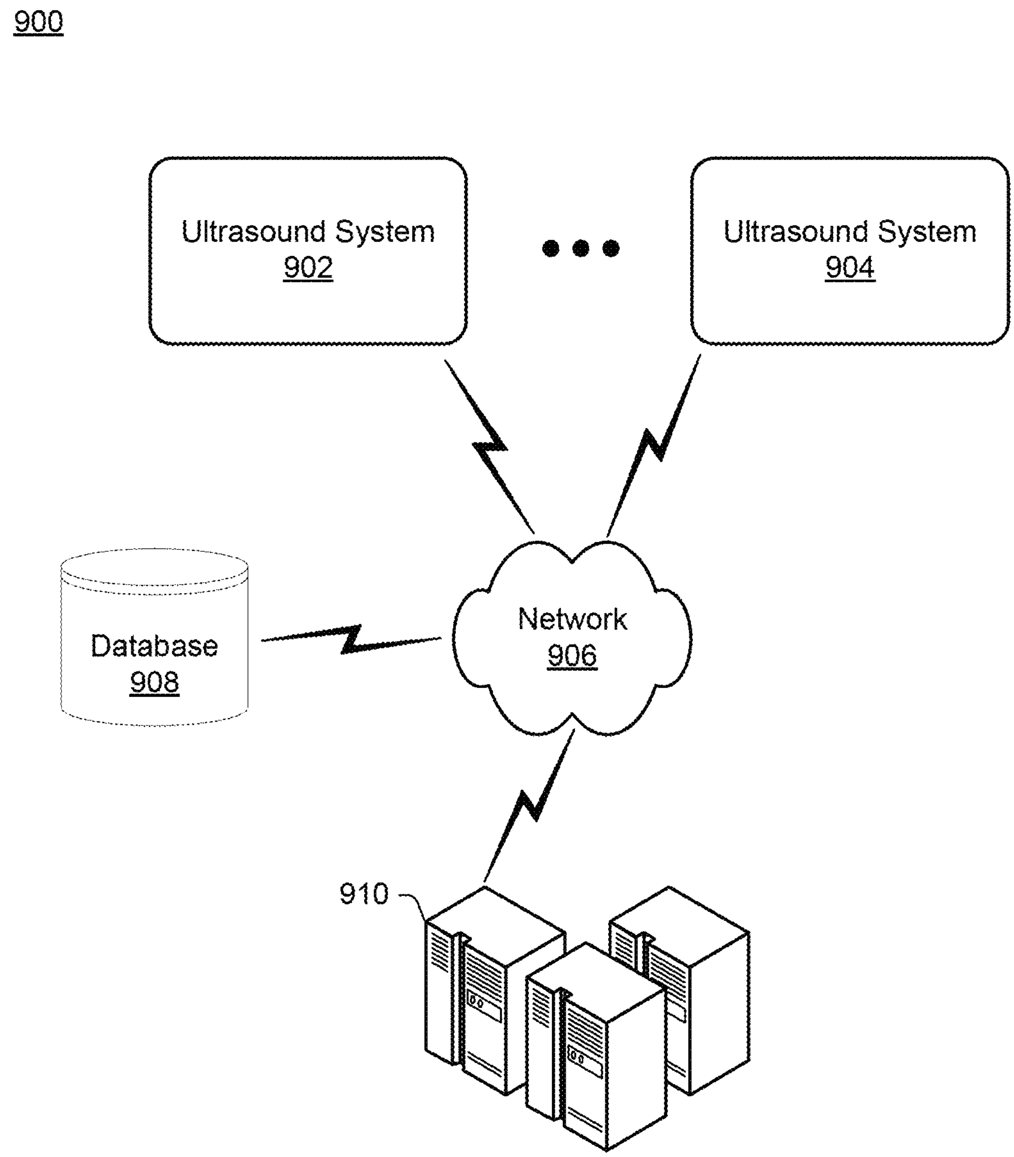
FIG. 9 illustrates an example environment for oral ultrasound in accordance with some embodiments.

FIG. 9 illustrates an environment 900 for an ultrasound system in accordance with some embodiments. Referring to FIG. 9, the environment 900 includes an ultrasound system 902 and an ultrasound system 904. Two example ultrasound systems 902 and 904 are illustrated in FIG. 9 for clarity. However, the environment 900 can include any suitable number of ultrasound systems, such as the ultrasound systems maintained by a care facility or the department of a care facility. Generally, an ultrasound system can include any suitable device (e.g., a component of an ultrasound system). Examples devices of the ultrasound systems 902 and 904 include a charging station, an ultrasound machine, a display device (e.g., a tablet or smartphone), an ultrasound scanner, and an ultrasound cart. Other examples include a transducer cable, a transducer cable holder, a docking station for an ultrasound machine, a scanner station configured to hold one or more ultrasound scanners, a needle guide, a battery for a wireless ultrasound scanner, a battery for an ultrasound machine, a registration system, and the like.

The ultrasound systems 902 and 904 can be in communication via the network 906 as part of the environment 900. The network 906 can include any suitable network, such as a local area network, a wide area network, a near field communication network, the Internet, an intranet, an extranet, a system bus that couples devices or device components (e.g., in an ASIC, FPGA, or SOC), and combinations thereof. Accordingly, in embodiments, information can be communicated to the ultrasound systems 902 and 904 through the network 906. For instance, the database 908 can store instructions executable by a processor system of the ultrasound systems 902 and 904, and communicate the instructions via the network 906. The database 908 can store ultrasound examination data as part of a medical archiver, e.g., a VNA and share the data with the ultrasound systems 902 and 904.

The environment 900 also includes a server system 910 that can implement any of the functions described herein. The server system 910 can be a separate device from the ultrasound systems 902 and 904. Alternatively, the server system 910 can be included in at least one of the ultrasound systems 902 and 904. In one example, the server system 910 and the database 908 are included in at least one of the ultrasound systems 902 and 904. In an example, the server system 910 is implemented as a remote server system that is remote from (e.g., not collocated with) the ultrasound systems 902 and 904.

Example Procedures

Figure 10:
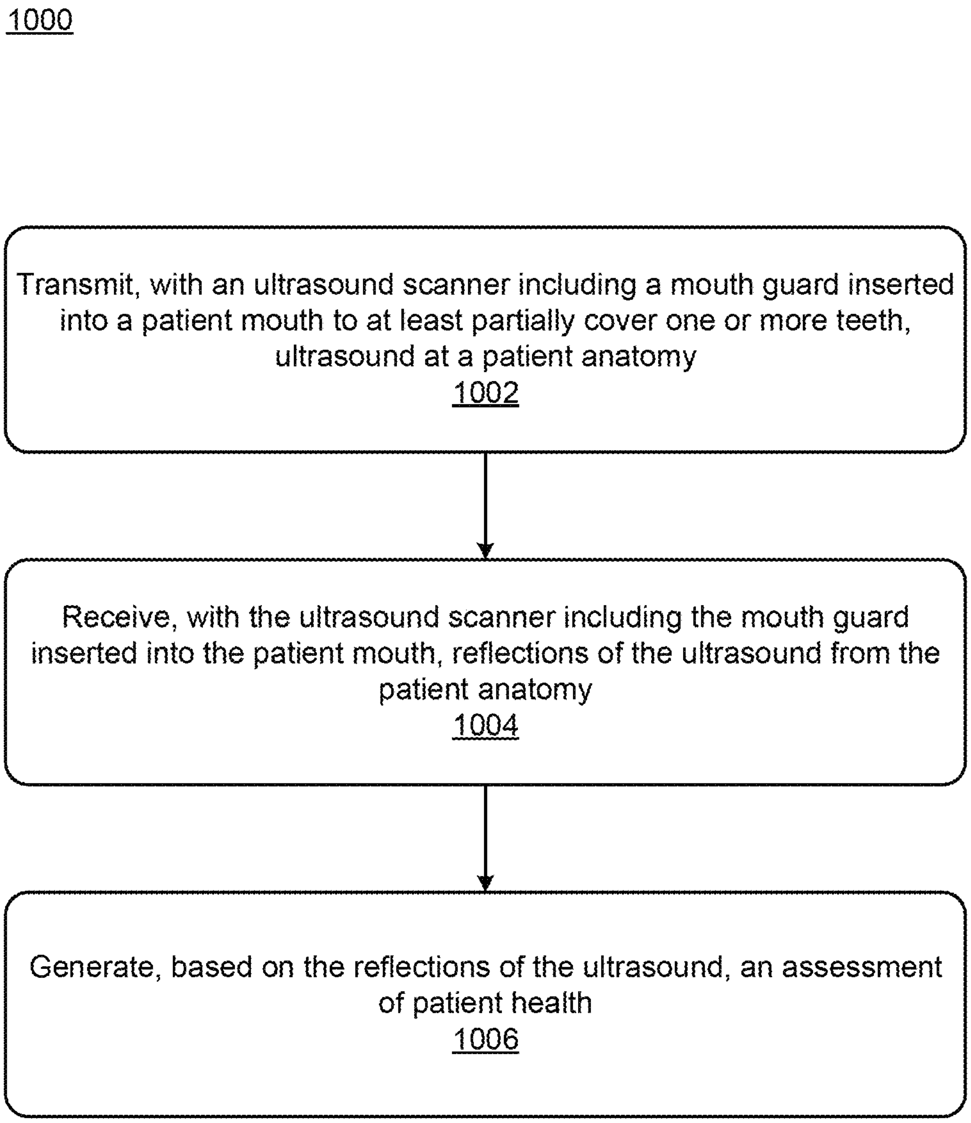
FIG. 10 illustrates an example method for oral ultrasound in accordance with some embodiments.

FIG. 10 illustrates an example method 1000 that can be implemented by an ultrasound system in accordance with some embodiments for oral ultrasound, e.g., the ultrasound systems 200, 300, or 400. The ultrasound system can include an ultrasound scanner (e.g., transducer or probe), an ultrasound machine, a processor system, and a display device. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 9.

Referring to FIG. 10, ultrasound is transmitted, with an ultrasound scanner including a mouth guard when inserted into a patient mouth to at least partially cover one or more teeth, at a patient anatomy (block 1002). Reflections of the ultrasound are received, with the ultrasound scanner including the mouth guard when inserted into the patient mouth, from the patient anatomy (block 1004). An assessment of patient health is generated based on the reflections of the ultrasound (block 1006).

In some embodiments, the patient anatomy includes the one or more teeth and a gum tissue, and the assessment of the patient health includes at least one recession amount of the gum tissue for the one or more teeth. The mouth guard can include an inner transducer array and an outer transducer array both configured for the transmission and the reception. The at least one recession amount can include one or more inner recession amounts based on the transmission and the reception from the inner transducer array and one or more outer recession amounts based on the transmission and the reception from the outer transducer array. The recession amounts can be included in a recession table. In some embodiments, a processor system implements a machine-learned model to generate the at least one recession amount.

In some embodiments, the patient anatomy includes the one or more teeth and the assessment of patient health includes a first image and a second image. The first image can include a first predicted appearance of the one or more teeth that results without an installation of orthodontia, and the second image can include a second predicted appearance of the one or more teeth that results with the installation of the orthodontia. In some embodiments, a processor system implements a machine-learned model to generate the first image and the second image.

In some embodiments of oral ultrasound, the patient anatomy includes a gum tissue and the assessment of the patient health includes an indication of a stiffness of the gum tissue. In some embodiments, the ultrasound scanner can use ultrasound (e.g., a series of push pulses) to induce a shear wave, and the processor system can determine a velocity of the resulting shear wave. Based on the velocity and Young's modulus, the processor system can determine the indication of the stiffness of the gum tissue, including an elastography determination.

In some embodiments, the patient anatomy includes the one or more teeth and the assessment of the patient health includes an indication of tooth enamel for the one or more teeth. The indication of the tooth enamel can include an enamel map with values representing at least one of enamel wear or remaining enamel.

In some embodiments, the patient anatomy includes the one or more teeth and bone that holds roots of the one or more teeth (e.g., the bone 328 in FIG. 3). The assessment of the patient health can include a recommendation to extract at least one tooth of the one or more teeth. Additionally or alternatively, the patient anatomy can include gum tissue touching the roots of the one or more teeth (e.g., the gum tissue 326 in FIG. 3), and the assessment of the patient health can include a health of the gum tissue. The recommendation can be based on the health of the gum tissue.

In some embodiments, the patient anatomy includes the one or more teeth and bone that holds roots of the one or more teeth (e.g., the bone 328 in FIG. 3), and the assessment of the patient health includes a score that indicates a health of the bone. For example, the score can be based on an amount of movement of the roots relative to the bone or a distance between the roots and the bone. The movement can be determined by the ultrasound system based on a patient history that includes previous examinations.

In some embodiments, the patient anatomy includes the one or more teeth and the assessment of the patient health includes a binary indicator (e.g., the binary indicator 412) that indicates if at least one tooth of the one or more teeth can support a crown procedure. The binary indicator can be displayed on a display device of the ultrasound system.

In some embodiments of oral ultrasound, the patient anatomy includes the one or more teeth. The mouth guard can include a first pocket configured to hold a transducer array (e.g., the pocket 504 that holds the transducer array 506 in FIG. 5). The mouth guard can also include a second pocket configured to hold a coupling agent that is positioned between the transducer array and the one or more teeth (e.g., the pocket 508 that holds the coupling agent 510 in FIG. 5). The coupling agent can be configured to couple the ultrasound from the transducer array to the one or more teeth. In some embodiments, the coupling agent includes a whitening agent configured to whiten the one or more teeth. Additionally or alternatively, the coupling agent can include a hardening agent that when activated by an activation source causes the coupling agent to harden into a mold of the one or more teeth. The processor system can be implemented to generate a three-dimensional (3D) model of the mold and a model of a (dental) bridge based on the 3D model. The activation source can include at least one of a heat gun, an ultraviolet light, and a chemical configured to be injected into the coupling agent.

In some embodiments, the patient anatomy includes the one or more teeth and bone that holds roots of the one or more teeth, and the one or more teeth have an orthodontia installed. The assessment of the patient health can include a recommended adjustment of the orthodontia (e.g., the adjustment table 318). In some embodiments, the processor system is implemented to determine an amount of movement of the roots relative to the bone or a distance between the roots and the bone. The amount of movement of the roots and/or the distance between the roots and the bone can be determined from imaging of the tissue (including through the tissue), and comparing the tissue imaging in current and previous oral ultrasound examinations. In some embodiments, the processor system is implemented to determine blood flow, tissue growth, and inflammation detection. The recommended adjustment can be based on at least one of the amount of the movement and the distance.

In some embodiments, the ultrasound system includes a registration system, and the mouth guard is deformable from a first shape to fit the patient mouth. In some embodiments, the registration system is implemented to determine one or more deformation amounts of the mouth guard when it is deformed from the first shape. The processor system can generate an ultrasound image based on the reflections of the ultrasound. The generation of the ultrasound image can include correction of distortion of the ultrasound image, based on the one or more deformation amounts associated with the distortion caused by the deforming of the mouth guard.

In some embodiments, the patient anatomy includes bone that holds roots of the one or more teeth, and the assessment of the patient health includes a score indicative of a health status of the bone to support a tooth implant. The score can be binary.

In some embodiments, if upon firing ultrasound at a patient anatomy (e.g., tooth), the patient reports a physiological response, e.g., heat, that is indicative of a problem, the ultrasound system can adjust the strength of the ultrasound being used on the patient. Such adjustments can be made to ensure that the oral ultrasound system is producing its results while also avoiding pain and/or injury to the patient.

In some embodiments, the mouth guard is battery powered. Having a battery-powered mouth guard prevents the patient from experiencing electrical shock from a wall outlet, e.g., 120 volts, 60 Hz power supply. Additionally or alternatively, the processor system can be powered by a battery. In an example, a same battery powers the mouth guard and the processor system.

Figure 11:
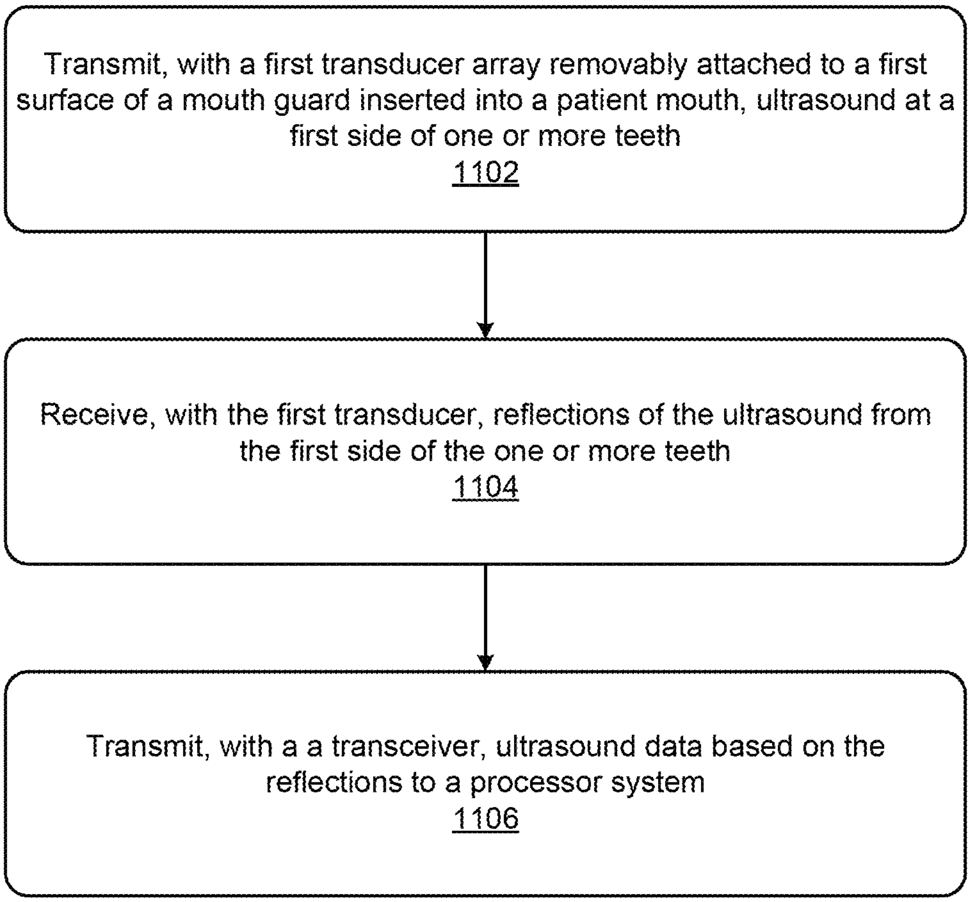
FIG. 11 illustrates another example method for oral ultrasound in accordance with some embodiments

FIG. 11 illustrates an example method 1100 that can be implemented by an ultrasound system, including one or more components of the ultrasound system (e.g., the ultrasound systems 200, 300, or 400) in accordance with some embodiments for oral ultrasound. For example, the method 1100 can be implemented by an ultrasound scanner (e.g., the one or more of the ultrasound scanners 104, 204, 302, and 402). In some embodiments, the ultrasound scanner is a patient-worn ultrasound scanner. The ultrasound system can include an ultrasound scanner (e.g., transducer or probe), an ultrasound machine, a processor system, and a display device. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 9.

Referring to FIG. 11, ultrasound is transmitted, with a first transducer array removably attached to a first surface of a mouth guard inserted into a patient mouth, at a first side of one or more teeth (block 1102). Reflections of the ultrasound are received, with the first transducer, from the first side of the one or more teeth (block 1104). Ultrasound data based on the reflections is transmitted to a processor system (block 1106).

In some embodiments, a patient-worn ultrasound system includes a second transducer array removably attached to a second surface of the mouth guard and configured to transmit additional ultrasound at a second side of the one or more teeth and receive additional reflections of the additional ultrasound from the second side of the one or more teeth, wherein the ultrasound data is based on the additional reflections. Additionally or alternatively, in some embodiments, the patient-worn ultrasound system includes a third transducer array removably attached to a third surface of the mouth guard and configured to transmit further ultrasound at a third side of the one or more teeth and receive further reflections of the further ultrasound from the third side of the one or more teeth, wherein the ultrasound data is based on the further reflections.

In some embodiments of oral ultrasound, the mouth guard can include a first pocket implemented to hold the first transducer array when the first transducer array is attached to the mouth guard. The first pocket can expose electrical connectors in the mouth guard configured to interface with the first transducer array and transfer data based on the reflections to the transceiver (e.g., as indicated in FIG. 5 with the connector 516 and the wire 518).

In some embodiments, the mouth guard includes a second pocket implemented to hold a coupling agent configured to couple the ultrasound to the first side of the one or more teeth. The second pocket can at least partially overlap the first pocket and be shallower than the first pocket.

In some embodiments of oral ultrasound, the mouth guard includes a stand implemented to attach to a pad containing a coupling agent configured to couple the ultrasound to the first side of the one or more teeth. The pad when attached to the stand can be implemented to cover the first transducer array (e.g., see FIG. 5).

In some embodiments, the mouth guard is disposable. Additionally or alternatively, one or more of the first transducer array, the second transducer array, and the third transducer array are not disposable, and instead can be cleaned according to a cleaning procedure and configured for reuse in a subsequent examination, e.g., by being attached to another mouth guard.

In some embodiments, the ultrasound system includes a cable connected to the transceiver on one end of the cable and to the processor system on another end of the cable. The cable can carry the ultrasound data transmitted by the transceiver. Additionally or alternatively, the cable can carry power to the mouth guard, e.g., from a battery power source.

In some embodiments, the mouth guard includes a shape memory alloy configured to deform the mouth guard from an original shape to fit the patient mouth when a first force is applied and return the mouth guard to the original shape when a second force is applied. In some embodiments, the at least one of the first force and the second force is caused by application of heat. Additionally or alternatively, at least one of the first force and the second force is caused by application of an electrical signal.

FIG. 12 illustrates an example method 1200 that can be implemented by an ultrasound system in accordance with some embodiments for oral ultrasound, e.g., the ultrasound systems 200, 300, or 400. The ultrasound system can include an ultrasound scanner (e.g., transducer or probe), an ultrasound machine, a processor system, and a display device. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 9.

Referring to FIG. 12, ultrasound is transmitted, with a patient-worn ultrasound scanner inserted into a patient mouth, at a patient anatomy (block 1202). Reflections of the ultrasound are received, with the ultrasound scanner, from the patient anatomy (block 1204). An assessment of patient health is generated based on the reflections of the ultrasound, the assessment of patient health including at least one of a recession amount of a gum tissue, a predictive image that predicts an appearance of one or more teeth based on an installation of orthodontia or a lack of the installation of the orthodontia, a recommended adjustment of the orthodontia, an indication of a stiffness of the gum tissue, an indication of tooth enamel for the one or more teeth, the indication of the tooth enamel indicating enamel wear or remaining enamel, a recommendation to extract at least one tooth of the one or more teeth, a score that indicates a health of a bone that holds roots of the one or more teeth, a score indicative of a health status of the bone to support a tooth implant, and an indicator that indicates if a tooth of the one or more teeth can support a crown procedure (block 1206).

In some embodiments, the method 1200 further includes generating an ultrasound image based on the reflections of the ultrasound. Generating the assessment of the patient health can include processing the ultrasound image with a machine-learned model.

Example Embodiments

Much of the disclosure above is described with respect to an ultrasound scanner with a mouth guard form factor that is suitable to image teeth, gum tissue, and bone holding the roots of the teeth. However, the techniques disclosed herein are not so limited to this form factor and these patient anatomies. For example, the ultrasound scanners 204-3-204-7 described with respect to FIG. 2 include means of articulation, such as through the operator's fingers or a mechanical articulation joint (e.g., the articulation joint 218). Accordingly, these ultrasound scanners can be manipulated inside a patient's mouth to image various patient anatomies, including a sinus cavity, septum, tonsils, cheek tissue, jaw muscles, Eustachian tube, etc. Hence, the ultrasound scanners 204-3-204-7 can be used for detection and treatment of various illnesses, such as tonsillitis, deviated septum, inflamed sinus tissue, temporomandibular joint disorder (TMJ), ear drainage issues, and the like. By using ultrasound rather than X-ray or CT to image these patient anatomies, the patient is spared cumulative, ionizing radiation. This is particularly important to patients that have been exposed to large amounts of radiation, such as patients that have undergone cancer treatment, pilots and flight crews, and the like. Further, some patient anatomies, including cartilage, septum, tissue, and unhealthy bone do not image well with X-ray, and ultrasound provides more detail in the resulting images. Moreover, by using the ultrasound scanner disclosed herein, use of an otoscope inserted through the patient's nostril can be avoided, thus significantly reducing the patient's discomfort.

There are a number of example embodiments described herein.

Example 1 is an ultrasound system having an ultrasound scanner including a mouth guard configured to, when inserted into a patient mouth to at least partially cover one or more teeth, transmit ultrasound at a patient anatomy and receive reflections of the ultrasound from the patient anatomy; and a processor system coupled to the ultrasound scanner and configured to generate, based on the reflections of the ultrasound, an assessment of patient health.

Example 2 is the ultrasound system of example 1 that may optionally include that the patient anatomy includes the one or more teeth and a gum tissue, and the assessment of the patient health includes at least one recession amount of the gum tissue for the one or more teeth.

Example 3 is the ultrasound system of example 2 that may optionally include that the mouth guard includes an inner transducer array and an outer transducer array both configured for the transmission and the reception, wherein the at least one recession amount includes one or more inner recession amounts based on the transmission and the reception from the inner transducer array and one or more outer recession amounts based on the transmission and the reception from the outer transducer array.

Example 4 is the ultrasound system of example 21 that may optionally include that the processor system implements a machine-learned model to generate the at least one recession amount.

Example 5 is the ultrasound system of example 1 that may optionally include that the patient anatomy includes the one or more teeth and the assessment of patient health includes a first image and a second image, the first image including a first predicted appearance of the one or more teeth that results without an installation of orthodontia, the second image including a second predicted appearance of the one or more teeth that results with the installation of the orthodontia.

Example 6 is the ultrasound system of example 5 that may optionally include that the processor system implements a machine-learned model to generate the first image and the second image.

Example 7 is the ultrasound system of example 1 that may optionally include that the patient anatomy includes a gum tissue and the assessment of the patient health includes an indication of a stiffness of the gum tissue.

Example 8 is the ultrasound system of example 1 that may optionally include that the patient anatomy includes the one or more teeth and the assessment of the patient health includes an indication of tooth enamel for the one or more teeth.

Example 9 is the ultrasound system of example 8 that may optionally include that the indication of the tooth enamel includes an enamel map with values representing at least one of enamel wear or remaining enamel.

Example 10 is the ultrasound system of example 1 that may optionally include that the patient anatomy includes the one or more teeth and bone that holds roots of the one or more teeth, and the assessment of the patient health includes a recommendation to extract at least one tooth of the one or more teeth.

Example 11 is the ultrasound system of example 10 that may optionally include that the patient anatomy includes gum tissue touching the roots of the one or more teeth, the assessment of the patient health includes a health of the gum tissue, and the recommendation is based on the health of the gum tissue.

Example 12 is the ultrasound system of example 1 that may optionally include that the patient anatomy includes the one or more teeth and bone that holds roots of the one or more teeth, and the assessment of the patient health includes a score that indicates a health of the bone.

Example 13 is the ultrasound system of example 12 that may optionally include that the score is based on an amount of movement of the roots relative to the bone or a distance between the roots and the bone.

Example 14 is the ultrasound system of example 1 that may optionally include that the patient anatomy includes the one or more teeth and the assessment of the patient health includes a binary indicator that indicates if at least one tooth of the one or more teeth can support a crown procedure.

Example 15 is the ultrasound system of example 1 that may optionally include that the patient anatomy includes the one or more teeth, the mouth guard includes a first pocket configured to hold a transducer array and a second pocket configured to hold a coupling agent that is positioned between the transducer array and the one or more teeth, the coupling agent configured to couple the ultrasound from the transducer array to the one or more teeth.

Example 16 is the ultrasound system of example 15 that may optionally include that the coupling agent includes a whitening agent configured to whiten the one or more teeth.

Example 17 is the ultrasound system of example 15 that may optionally include that the coupling agent includes a hardening agent that when activated by an activation source causes the coupling agent to harden into a mold of the one or more teeth.

Example 18 is the ultrasound system of example 17 that may optionally include that the processor system is implemented to generate a three-dimensional (3D) model of the mold and a model of a bridge based on the 3D model.

Example 19 is the ultrasound system of example 17 that may optionally include that the activation source includes at least one of a heat gun, an ultraviolet light, and a chemical configured to be injected into the coupling agent.

Example 20 is the ultrasound system of example 1 that may optionally include that the patient anatomy includes the one or more teeth and bone that holds roots of the one or more teeth, the one or more teeth have an orthodontia installed, and the assessment of the patient health includes a recommended adjustment of the orthodontia.

Example 21 is the ultrasound system of example 20 that may optionally include that the processor system is implemented to determine an amount of movement of the roots relative to the bone or a distance between the roots and the bone, and the recommended adjustment is based on at least one of the amount of the movement and the distance.

Example 22 is the ultrasound system of example 1 that may optionally include a registration system, wherein the mouth guard is deformable from a first shape to fit the patient mouth and the registration system is implemented to determine one or more deformation amounts of the mouth guard when it is deformed from the first shape.

Example 23 is the ultrasound system of example 22 that may optionally include that the processor system is implemented to generate an ultrasound image based on the reflections of the ultrasound, the generation of the ultrasound image including to correct, based on the one or more deformation amounts, distortion caused by the deforming of the mouth guard.

Example 24 is the ultrasound system of example 1 that may optionally include that the patient anatomy includes bone that holds roots of the one or more teeth, and the assessment of the patient health includes a score indicative of a health status of the bone to support a tooth implant.

Example 25 is the ultrasound system of example 24 that may optionally include that the score is binary.

Example 26 is the ultrasound system of example 1 that may optionally include that the mouth guard is battery powered.

Example 27 is a patient-worn ultrasound scanner having: a mouth guard configured for insertion into a patient mouth; a first transducer array removably attached to a first surface of the mouth guard and configured to transmit ultrasound at a first side of one or more teeth and receive reflections of the ultrasound from the first side of the one or more teeth; and a transceiver configured to transmit ultrasound data based on the reflections to a processor system.

Example 28 is the ultrasound scanner of example 27 that may optionally include a second transducer array removably attached to a second surface of the mouth guard and configured to transmit additional ultrasound at a second side of the one or more teeth and receive additional reflections of the additional ultrasound from the second side of the one or more teeth, wherein the ultrasound data is based on the additional reflections.

Example 29 is the ultrasound scanner of example 28 that may optionally include a third transducer array removably attached to a third surface of the mouth guard and configured to transmit further ultrasound at a third side of the one or more teeth and receive further reflections of the further ultrasound from the third side of the one or more teeth, wherein the ultrasound data is based on the further reflections.

Example 30 is the ultrasound scanner of example 27 that may optionally include that the mouth guard includes a first pocket implemented to hold the first transducer array when the first transducer array is attached to the mouth guard, the first pocket exposing electrical connectors in the mouth guard configured to interface with the first transducer array and transfer data based on the reflections to the transceiver.

Example 31 is the ultrasound scanner of example 30 that may optionally include that the mouth guard includes a second pocket implemented to hold a coupling agent configured to couple the ultrasound to the first side of the one or more teeth, the second pocket at least partially overlapping the first pocket and being shallower than the first pocket.

Example 32 is the ultrasound scanner of example 27 that may optionally include that the mouth guard includes a stand implemented to attach to a pad containing a coupling agent configured to couple the ultrasound to the first side of the one or more teeth, the pad when attached to the stand implemented to cover the first transducer array.

Example 33 is the ultrasound scanner of example 27 that may optionally include that the mouth guard is disposable.

Example 34 is the ultrasound scanner of example 27 that may optionally include a cable connected to the transceiver on one end of the cable and to the processor system on another end of the cable, the cable configured to carry the ultrasound data transmitted by the transceiver.

Example 35 is the ultrasound scanner of example 27 that may optionally include that the mouth guard comprises a shape memory alloy configured to deform the mouth guard from an original shape to fit the patient mouth when a first force is applied and return the mouth guard to the original shape when a second force is applied.

Example 36 is the ultrasound scanner of example 35 that may optionally include that at least one of the first force and the second force is caused by application of heat.

Example 37 is the ultrasound scanner of example 35 that may optionally include that at least one of the first force and the second force is caused by application of an electrical signal.

Example 38 is a method having operations that include inserting a patient-worn ultrasound scanner into a patient mouth; transmitting, with the ultrasound scanner, ultrasound at a patient anatomy; receiving, with the ultrasound scanner, reflections of the ultrasound from the patient anatomy; and generating, based on the reflections of the ultrasound, an assessment of patient health. In some embodiments, the assessment of patient health includes at least one of: a recession amount of a gum tissue; a predictive image that predicts an appearance of one or more teeth based on an installation of orthodontia or a lack of the installation of the orthodontia; a recommended adjustment of the orthodontia; an indication of a stiffness of the gum tissue; an indication of tooth enamel for the one or more teeth, where the indication of the tooth enamel indicates enamel wear or remaining enamel; a recommendation to extract at least one tooth of the one or more teeth; a score that indicates a health of a bone that holds roots of the one or more teeth; a score indicative of a health status of the bone to support a tooth implant; and an indicator that indicates if a tooth of the one or more teeth can support a crown procedure.

Example 39 is the ultrasound scanner of example 38 that may optionally include that generating an ultrasound image based on the reflections of the ultrasound, wherein the generating the assessment of the patient health includes processing the ultrasound image with a machine-learned model.

Example 40 is an ultrasound system that performs the operations of one or more of examples 38-39.

Example 41 is a method including the operations performed by the ultrasound system of one or more of examples 1-37.

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in some embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

We claim:

1. An ultrasound system comprising:
- an ultrasound scanner including a mouth guard configured to, when inserted into a patient mouth to at least partially cover one or more teeth, transmit ultrasound at a patient anatomy and receive reflections of the ultrasound from the patient anatomy, the mouth guard comprising a first surface, a sidewall and a second sidewall opposite to the first sidewall on the first surface that are configured to hold a first transducer array, the mouth guard further comprising a third sidewall and a fourth sidewall opposite to the third sidewall that are configured to hold a coupling agent, wherein the third sidewall is above the first sidewall and the fourth sidewall is above the second sidewall on the first surface, so that the coupling agent covers the first transducer array and is positioned between the first transducer array and the one or more teeth, and
- a processor system coupled to the ultrasound scanner and configured to generate, based on the reflections of the ultrasound, an assessment of patient health, wherein the patient anatomy includes a gum tissue and the assessment of the patient health includes an indication of a stiffness of the gum tissue.

2. The ultrasound system as described in claim 1, wherein assessment of the patient health includes at least one recession amount of the gum tissue for the one or more teeth, wherein the mouth guard comprises a second surface opposite to the first surface, wherein the second surface includes a third pocket configured to hold a second transducer array, wherein the first transducer array is an inner transducer array and the second transducer array is an outer transducer array wherein the first transducer array and the second transducer array are configured for transmission of the ultrasound and reception of the reflections of the ultrasound, wherein the at least one recession amount includes one or more inner recession amounts based on the transmission and the reception from the inner transducer array and one or more outer recession amounts based on the transmission and the reception from the outer transducer array.

3. The ultrasound system as described in claim 1, wherein the patient anatomy includes the one or more teeth and the assessment of patient health includes a first image and a second image, the first image including a first predicted appearance of the one or more teeth that results without an installation of orthodontia, the second image including a second predicted appearance of the one or more teeth that results with the installation of the orthodontia.

4. The ultrasound system as described in claim 1, wherein the patient anatomy includes the one or more teeth and the assessment of the patient health includes an indication of tooth enamel for the one or more teeth.

5. The ultrasound system as described in claim 1, wherein the patient anatomy includes the one or more teeth and bone that holds roots of the one or more teeth, and the assessment of the patient health includes a recommendation to extract at least one tooth of the one or more teeth.

6. The ultrasound system as described in claim 1, wherein the patient anatomy includes the one or more teeth and bone that holds roots of the one or more teeth, and the assessment of the patient health includes a score that indicates a health of the bone, and wherein the score is based on an amount of movement of the roots relative to the bone or a distance between the roots and the bone.

7. The ultrasound system as described in claim 1, wherein the patient anatomy includes the one or more teeth and the assessment of the patient health includes a binary indicator that indicates if at least one tooth of the one or more teeth can support a crown procedure.

8. The ultrasound system as described in claim 1, wherein the coupling agent is configured to couple the ultrasound from the first transducer array to the one or more teeth.

9. The ultrasound system as described in claim 1, wherein the patient anatomy includes the one or more teeth and bone that holds roots of the one or more teeth, the one or more teeth have an orthodontia installed, and the assessment of the patient health includes a recommended adjustment of the orthodontia, wherein the processor system is implemented to determine an amount of movement of roots relative to the bone or a distance between the roots and the bone, and the recommended adjustment is based on at least one of the amount of the movement and the distance.

10. The ultrasound system as described in claim 1, further comprising a registration system, wherein the mouth guard is deformable from a first shape to fit the patient mouth and the registration system is implemented to determine one or more deformation amounts of the mouth guard when it is deformed from the first shape, and further wherein the processor system is implemented to generate an ultrasound image based on the reflections of the ultrasound, the generation of the ultrasound image including to correct, based on the one or more deformation amounts, distortion caused by the deforming of the mouth guard.

11. The ultrasound system as described in claim 1, wherein the patient anatomy includes bone that holds roots of the one or more teeth, and the assessment of the patient health includes a score indicative of a health status of the bone to support a tooth implant.

12. The ultrasound system as described in claim 1, wherein the coupling agent includes a hardening agent that when activated by an activation source causes the coupling agent to harden into a mold.

13. The ultrasound system as described in claim 1, wherein the assessment of patient health includes a map of a patient oral anatomy, and wherein the processor system implements a machine-learned model to generate the map of the patient anatomy, wherein the map of the patient anatomy includes at least one of a recession map or an enamel map.

14. The ultrasound system as described in claim 1, wherein the first surface includes a first pocket comprising the first sidewall and the second sidewall, and a second pocket comprising third sidewall and the fourth sidewall, wherein the second pocket is shallower than the first pocket.

15. The patient-worn ultrasound scanner as described in claim 1, wherein each of the third sidewall and the fourth sidewall is a stand attached to the first surface.

16. A patient-worn ultrasound scanner comprising:
- a mouth guard comprising a first surface and a second surface opposite to the first surface that is configured for insertion into a patient mouth;
- a first transducer array removably attached to the first surface of the mouth guard and configured to transmit ultrasound at a first side of one or more teeth and receive reflections of the ultrasound from the first side of the one or more teeth, wherein the mouth guard includes a first sidewall and a second sidewall opposite to the first sidewall on the first surface that are implemented to hold the first transducer array, the mouth guard further comprising a third sidewall on the first surface and a fourth sidewall on the first surface opposite to the third sidewall that are implemented to hold a coupling agent, wherein the third sidewall is on the first surface above the first sidewall and the fourth sidewall is on the first surface above the second sidewall, so that the coupling agent covers the first transducer array and is positioned between the first transducer array and the first side of the one or more teeth; and a transceiver configured to transmit ultrasound data based on the reflections to a processor system.

17. The patient-worn ultrasound scanner as described in claim 16, further comprising a second transducer array removably attached to the second surface of the mouth guard and configured to transmit additional ultrasound at a second side of the one or more teeth and receive additional reflections of the additional ultrasound from the second side of the one or more teeth, wherein the ultrasound data is based on the additional reflections.

18. The patient-worn ultrasound scanner as described in claim 16, wherein the first pocket is configured to expose electrical connectors in the mouth guard configured to interface with the first transducer array and transfer data based on the reflections to the transceiver.

19. The patient-worn ultrasound scanner as described in claim 16 wherein the mouth guard is configured to enable insertion of and coupling to a second transducer array, which is different in size than the first transducer array.

20. A method comprising:

inserting a patient-worn ultrasound scanner including a mouth guard into a patient mouth;

transmitting, with the mouth guard, ultrasound at a patient anatomy;

receiving, with the mouth guard, reflections of the ultrasound from the patient anatomy, the mouth guard comprising a first surface, a first sidewall and a second sidewall opposite to the first sidewall on the first surface that are configured to hold a first transducer array, the mouth guard comprising a third sidewall and a fourth sidewall opposite to the third sidewall that are configured to hold a coupling agent, wherein the third sidewall is above the first sidewall and the fourth sidewall is above the second sidewall on the first surface, so that the coupling agent covers the first transducer array and is positioned between the first transducer array and the one or more teeth; and generating, based on the reflections of the ultrasound, an assessment of patient health that includes an indication of a stiffness of the gum tissue.

21. The method as described in claim 20, further comprising generating an ultrasound image based on the reflections of the ultrasound, wherein the generating the assessment of the patient health includes processing the ultrasound image with a machine-learned model.

* * * * *